United States Patent
Su et al.

(10) Patent No.: US 12,247,090 B2
(45) Date of Patent: Mar. 11, 2025

(54) ENZYME-MEDIATED FREE RADICAL INITIATING SYSTEMS FOR THE PRODUCTION OF HYDROGELS AND CONTROLLED RADICAL POLYMERIZATION PROCESSES

(71) Applicant: Duke University, Durham, NC (US)

(72) Inventors: Teng Su, Durham, NC (US); Jennifer West, Durham, NC (US); Neica Joseph, Durham, NC (US)

(73) Assignee: Duke University, Durham, NC (US)

( * ) Notice: Subject to any disclaimer, the term of this patent is extended or adjusted under 35 U.S.C. 154(b) by 349 days.

(21) Appl. No.: 17/812,354

(22) Filed: Jul. 13, 2022

(65) Prior Publication Data

US 2023/0026615 A1     Jan. 26, 2023

Related U.S. Application Data

(60) Provisional application No. 63/221,057, filed on Jul. 13, 2021.

(51) Int. Cl.
| | |
|---|---|
| *C08F 2/16* | (2006.01) |
| *C08F 22/10* | (2006.01) |
| *C08J 3/075* | (2006.01) |
| *C08K 3/20* | (2006.01) |
| *C08K 5/00* | (2006.01) |
| *C08K 5/3417* | (2006.01) |
| *C12P 7/625* | (2022.01) |

(52) U.S. Cl.
CPC ............ *C08F 2/16* (2013.01); *C08F 22/1006* (2020.02); *C08J 3/075* (2013.01); *C08K 3/20* (2013.01); *C08K 5/0025* (2013.01); *C08K 5/3417* (2013.01); *C12P 7/625* (2013.01); *C08J 2333/08* (2013.01); *C12Y 111/01007* (2013.01)

(58) Field of Classification Search
CPC ......... C08F 2/16; C08F 22/1006; C08J 3/075; C08J 2333/08; C12Y 111/01007; C12P 7/625; C08K 3/20; C08K 5/0025; C08K 5/3417
See application file for complete search history.

(56) References Cited

U.S. PATENT DOCUMENTS

| | | | |
|---|---|---|---|
| 10,166,314 B2 | 1/2019 | Phopase et al. | |
| 2011/0305872 A1* | 12/2011 | Li | C08F 291/00 428/141 |
| 2020/0230288 A1 | 7/2020 | Cho et al. | |

FOREIGN PATENT DOCUMENTS

| WO | WO 2009/148405 | 12/2009 |
|---|---|---|
| WO | WO 2019/043547 | 3/2019 |

OTHER PUBLICATIONS

Attieh et al., Enzyme-Initiated Free-Radical Polymerization of Molecularly Imprinted Polymer Nanogels on a Solid Phase with an Immobilized Radical Source. Angew. Chem. Int. Ed. 2017; 56(12):3339-3343.

(Continued)

*Primary Examiner* — Robert D Harlan
(74) *Attorney, Agent, or Firm* — Casimir Jones, S.C.; Anne M. Reynolds

(57) ABSTRACT

The present disclosure describes, in part, an enzyme-mediated radical initiating system and methods of using the system to produce polymers, including polymeric hydrogels, at ambient conditions.

20 Claims, 27 Drawing Sheets

(56) References Cited

OTHER PUBLICATIONS

Bae et al., Horseradish peroxidase-catalysed in situ-forming hydrogels for tissue-engineering applications. J. Tissue Eng. Regen. Med. 2015/ 9(11):1125-1232.

Darabi et al., Nitroxide-Mediated Polymerization of 2-(Diethylamoino)ethyl Methacrylate (DEAEMA) in Water. Macromolecules, 2015, 48(1), 72-80.

Durand et al., Enzyme-mediated initiation of acrylamide polymerization: reaction mechanism. Polymer, 2000, 41(23), 8183-8192.

Kohri, Development of HRP-mediated enzymatic polymerization under heterogeneous conditions for the preparation of functional particles. Plym. J., 2014, 49(7), 373-380.

Su et al., Cardiac Stem Cell Patch Integrated with Microengineered Blood Vessels Promotes Cardiomyocyte Proliferation and Neovascularization after Acute Myocardial Infarction. ACS Appl. Mater. Interfaces, 2018, 10, 33088-33096.

Su et al., HRP-mediated polymerization forms tough nanocomposite hydrogels with high biocatalytic performance. Chem Commun (Camb). Sep. 21, 2013;49(73):8033-5.

Ullah et al., Classification, processing and application of hydrogels: A review. Mater Sci Eng C Mater Biol Appl. Dec. 1, 2015;57:414-33.

Zhang et al., Enzyme-Initiated Reversible Addition-Fragmentation Chain Transfer Polymerization. Macromolecules, 2015, 48, 7792-7802.

* cited by examiner

FIGS. 5A-5D
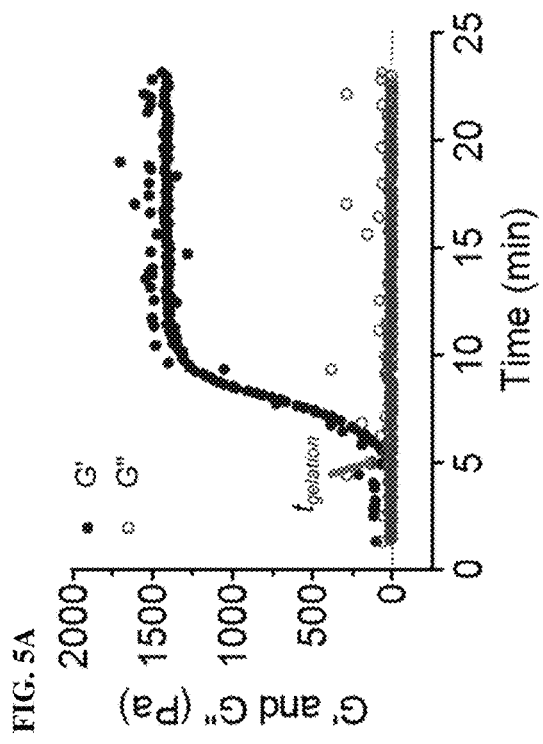
FIG. 5A
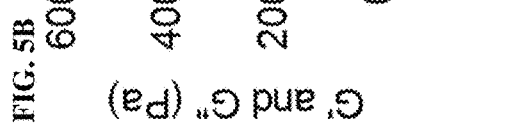
FIG. 5B
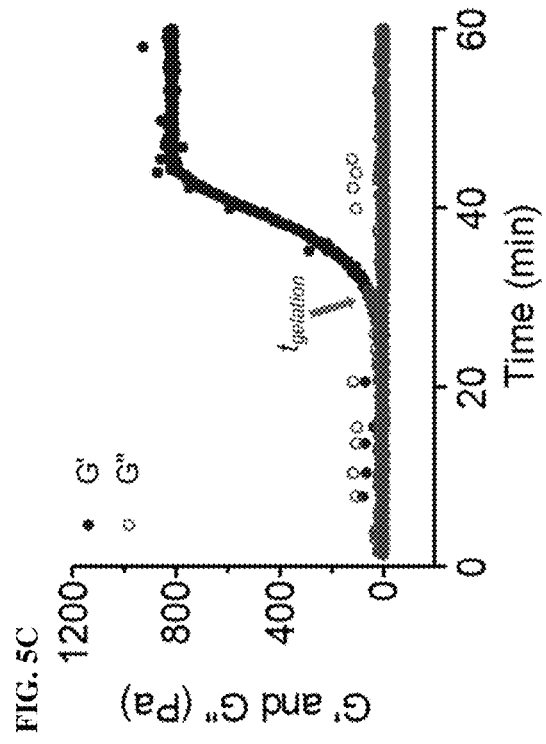
FIG. 5C
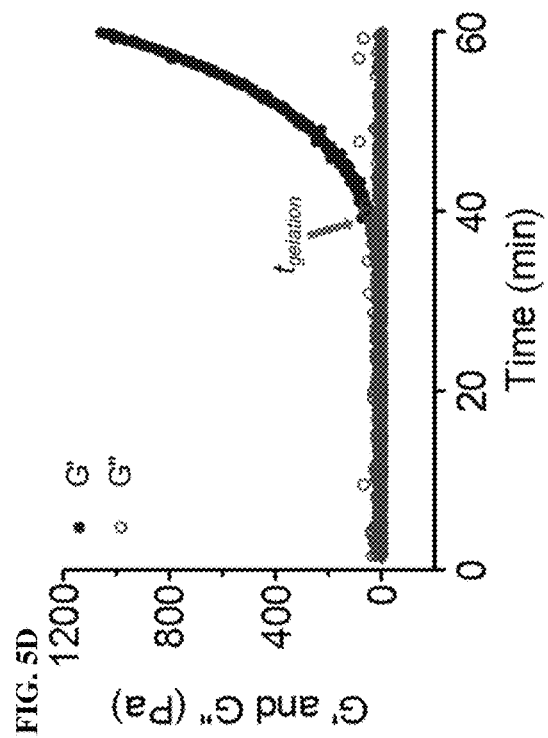
FIG. 5D

FIGS. 9A-9B
FIG. 9A
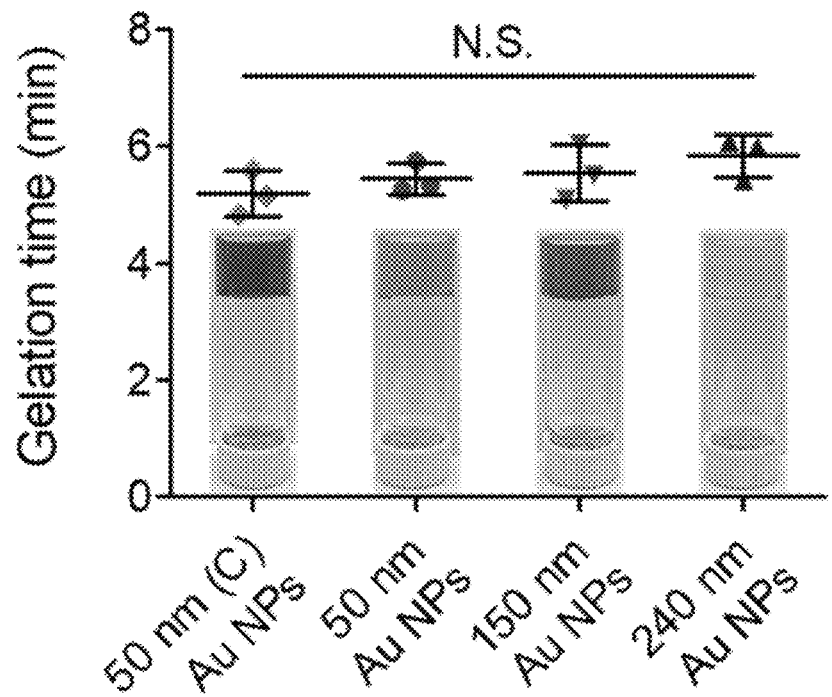
FIG. 9B
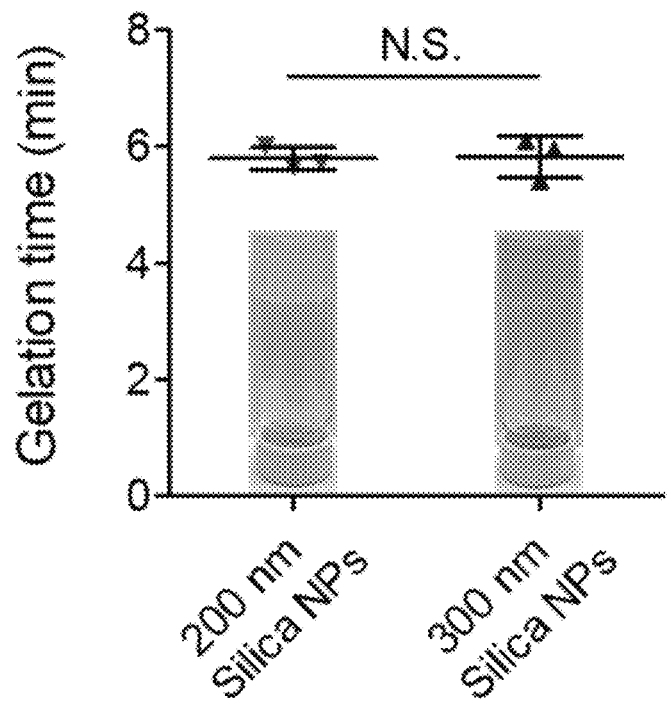

FIGS. 10A-10B
FIG. 10A
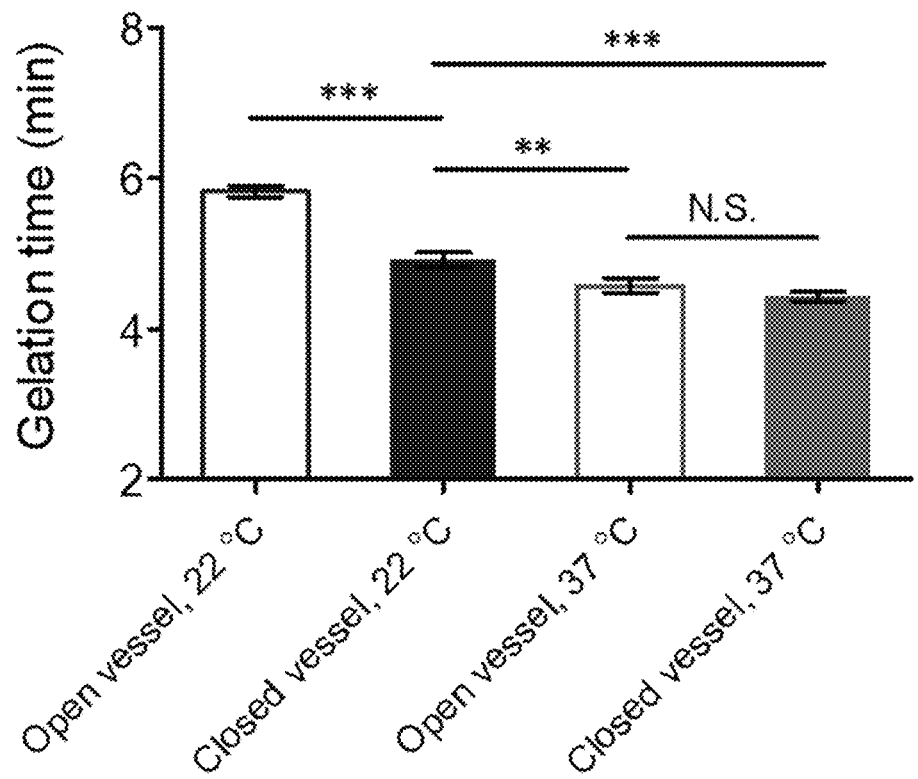
FIG. 10B
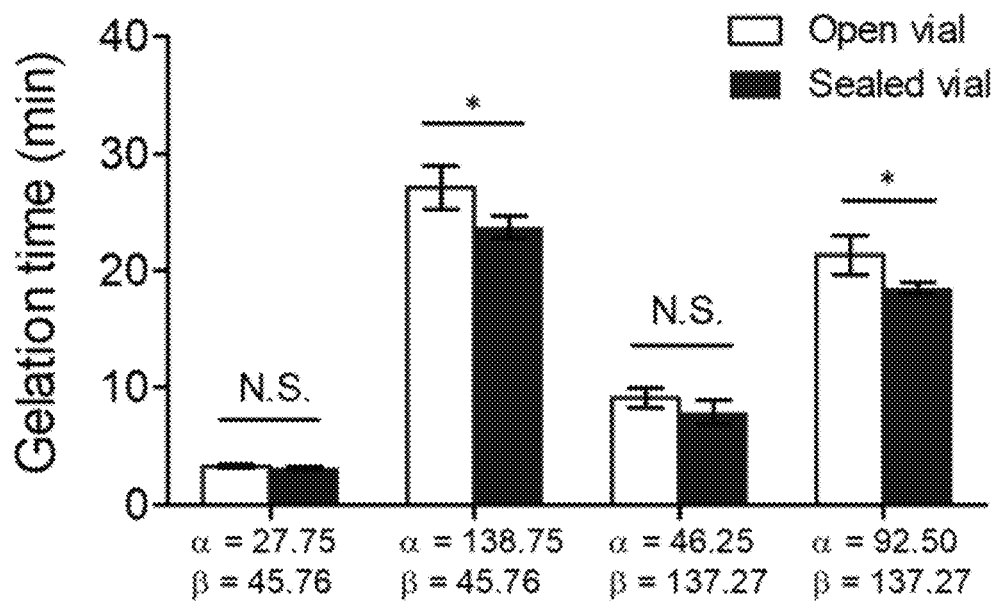

FIG. 13A (+) Control

FIG. 13B (-) Control

FIG. 13C A-Gel

FIG. 13D H-Gel

FIGS. 14A-14F
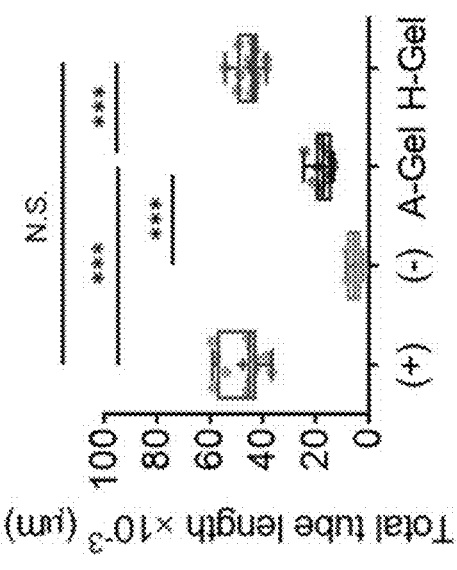
FIG. 14A
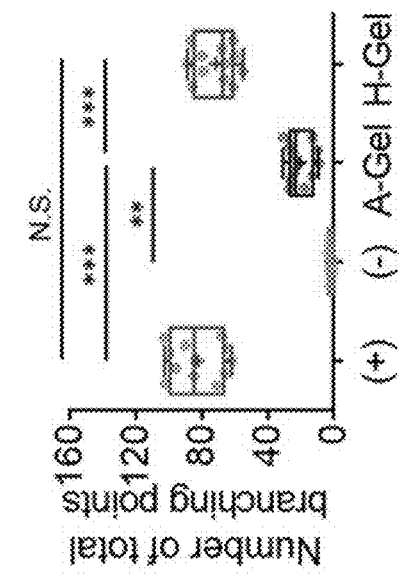
FIG. 14B
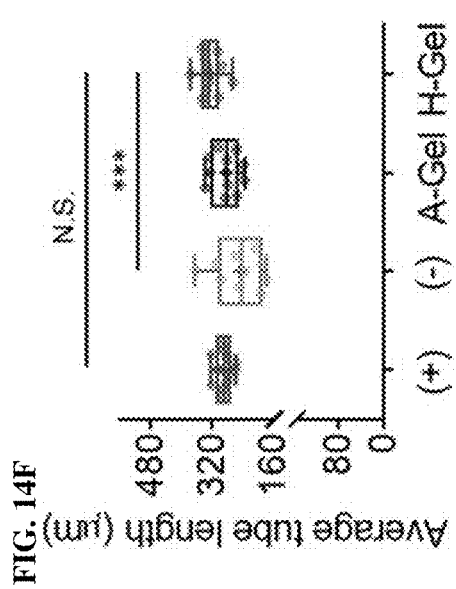
FIG. 14C
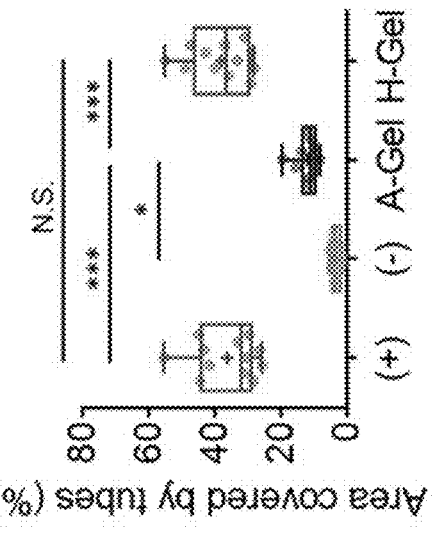
FIG. 14D
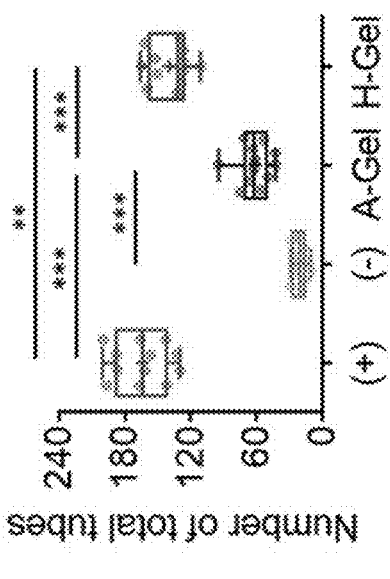
FIG. 14E
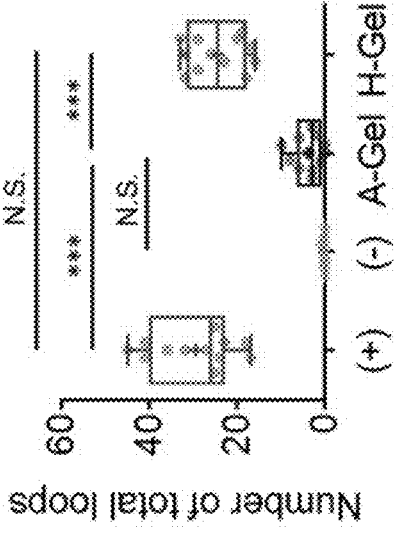
FIG. 14F FIGS. 16A-16C
FIG. 16A
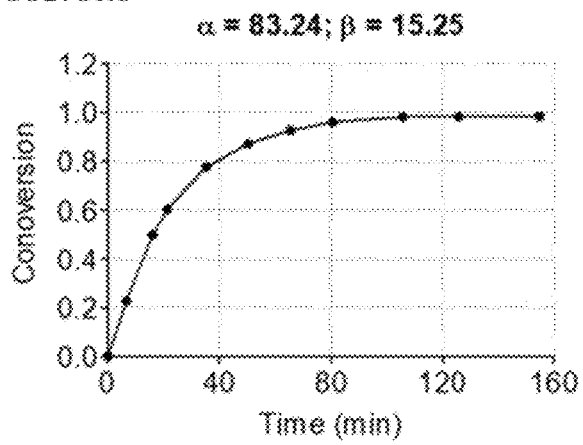 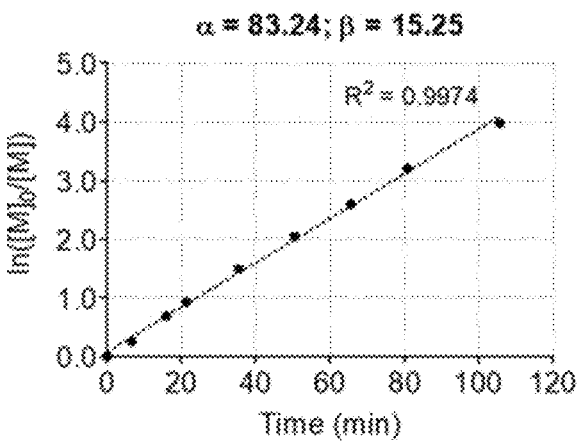
FIG. 16B
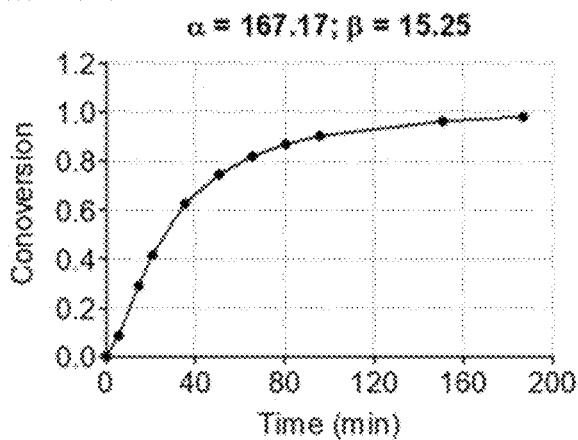 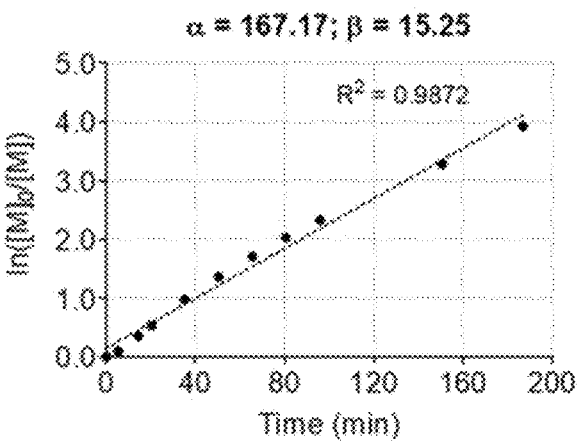
FIG. 16C
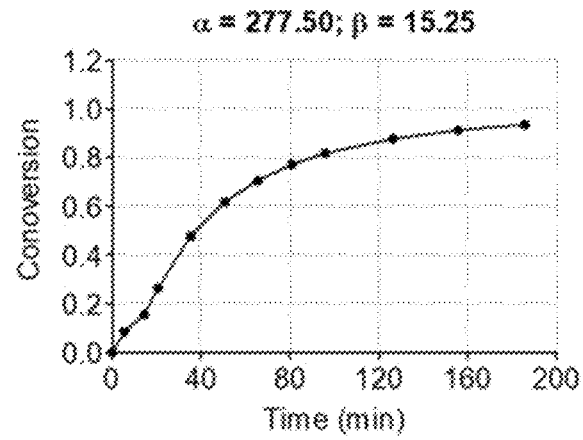 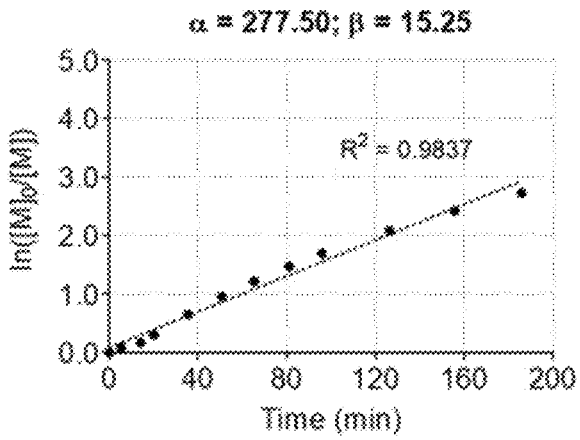

FIGS. 17A-17B
FIG. 17A
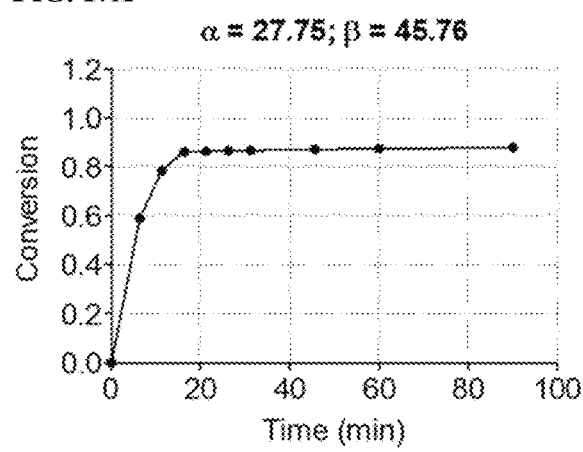
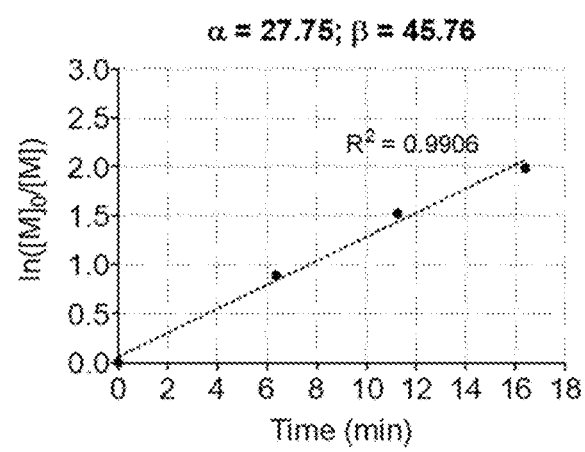
FIG. 17B
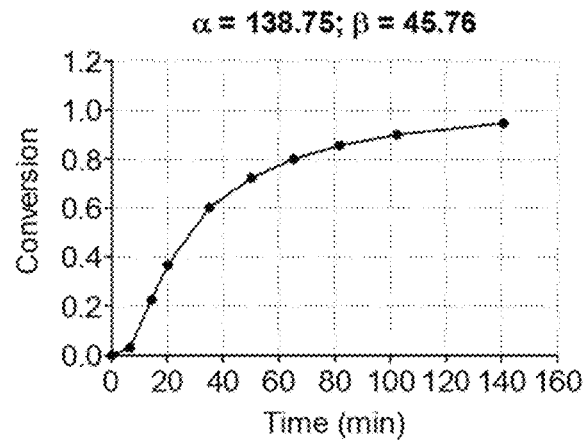
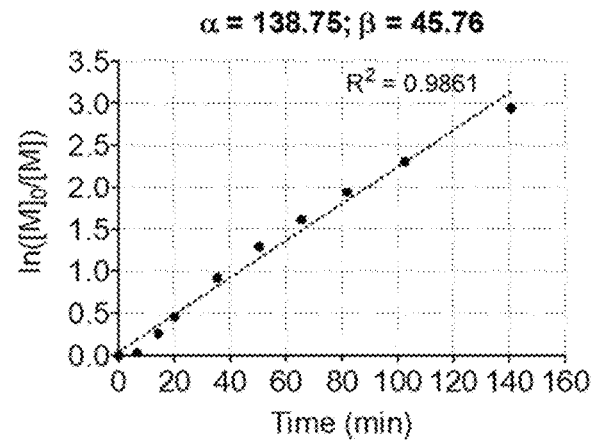

FIGS. 17C-17D
FIG. 17C
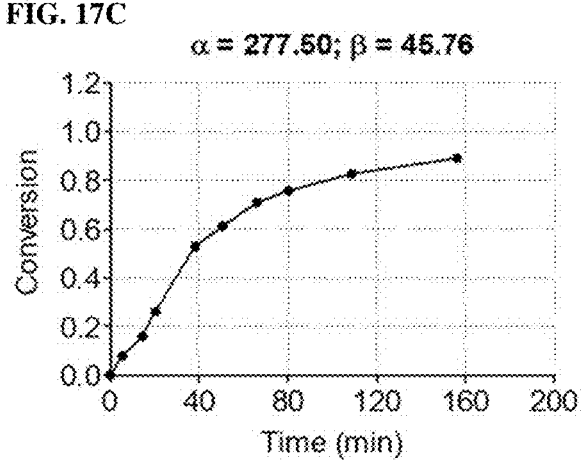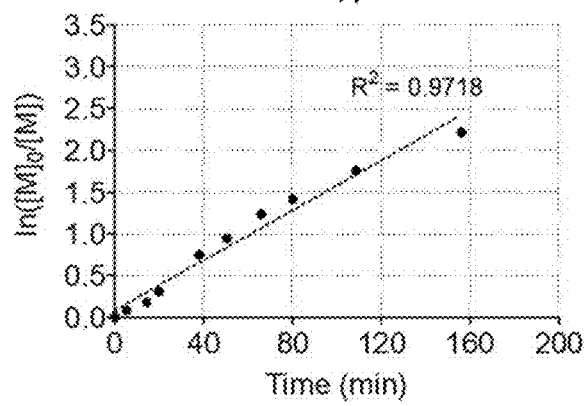
FIG. 17D
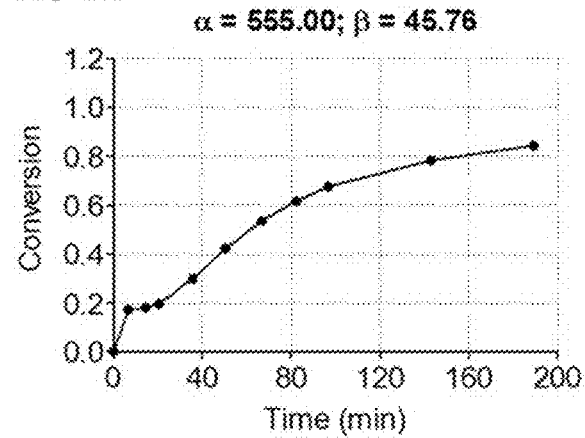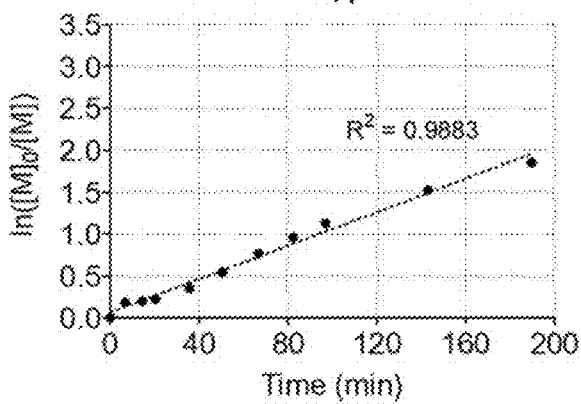

FIGS. 18A-18B
FIG. 18A
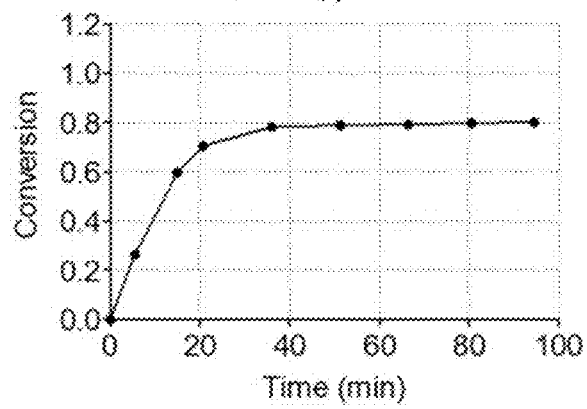
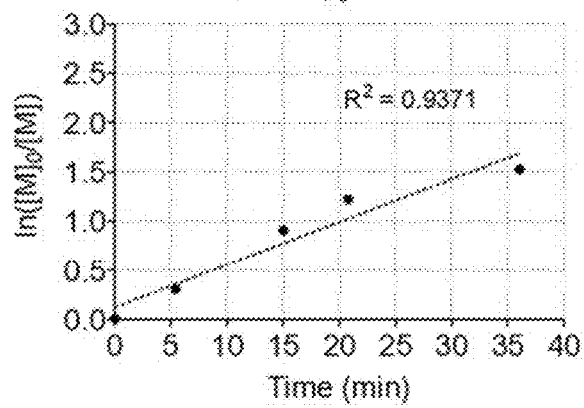
FIG. 18B
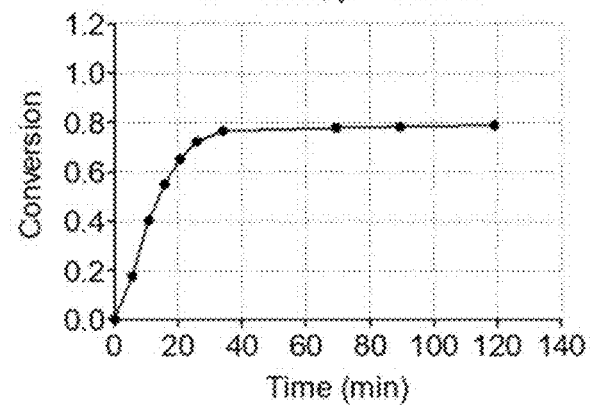
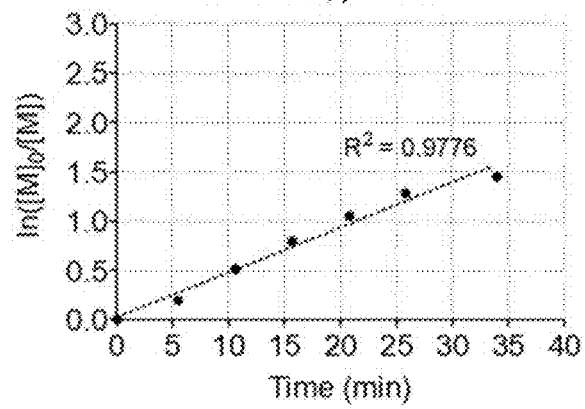

FIGS. 18C-18D
FIG. 18C
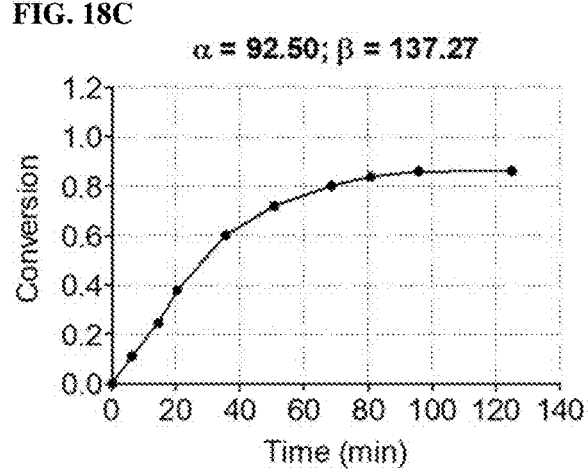 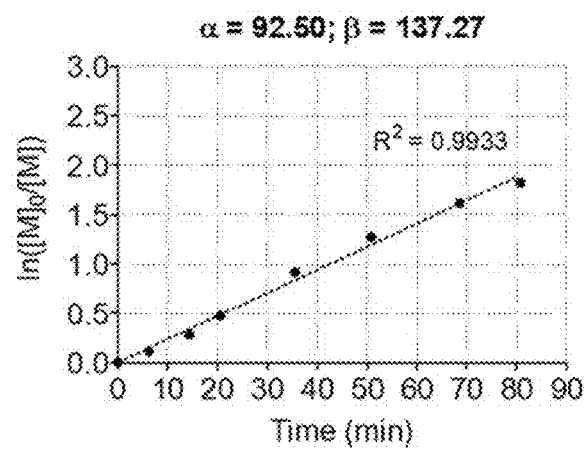
FIG. 18D
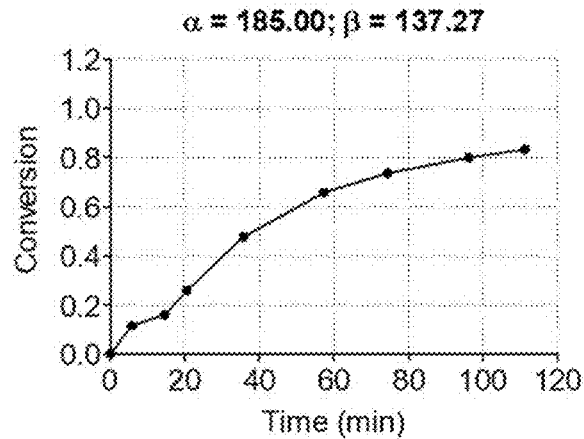 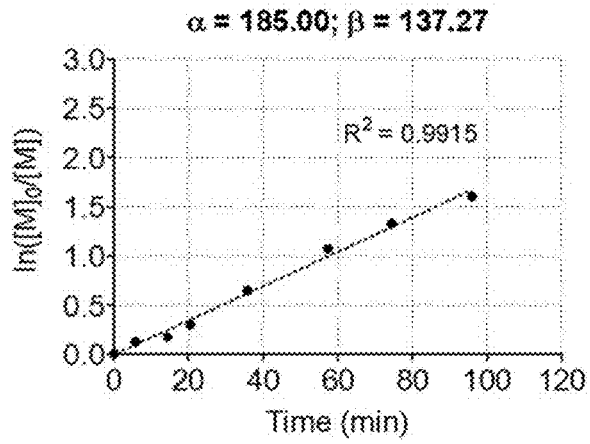

FIGS. 19A-19C
FIG. 19A
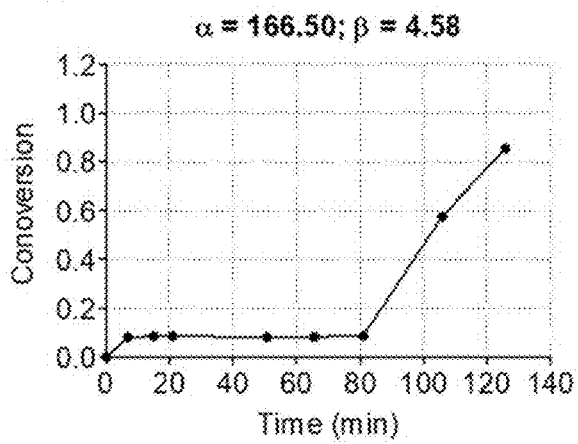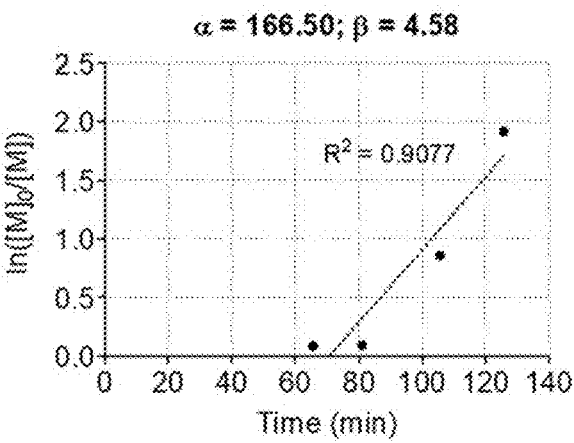
FIG. 19B
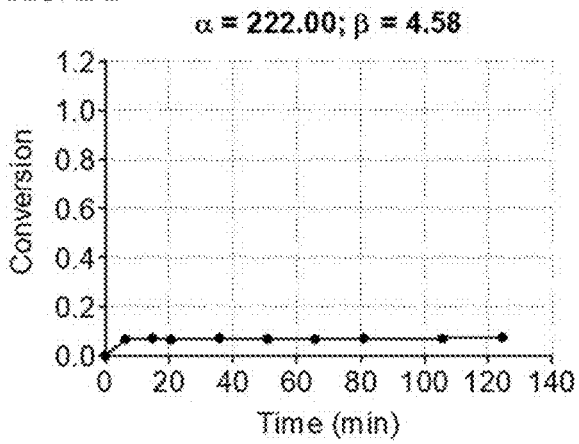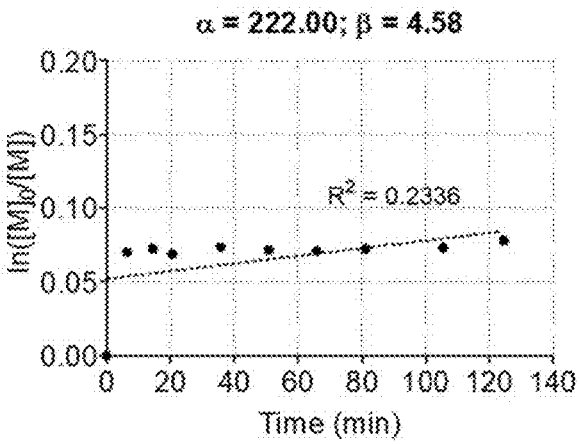
FIG. 19C
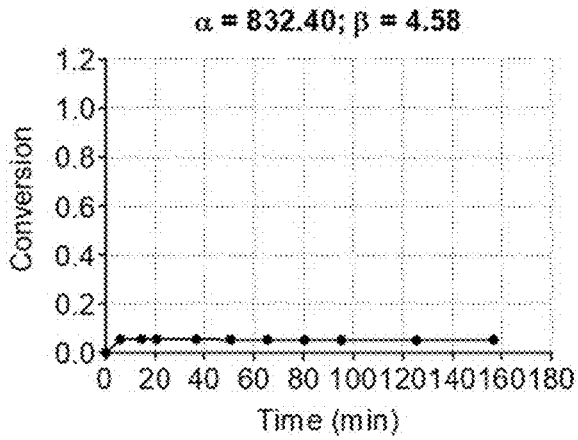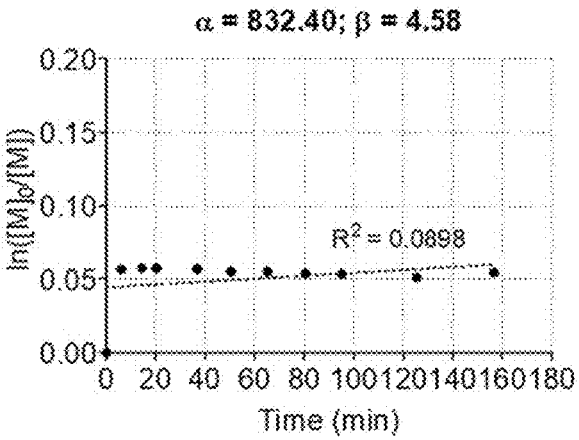

FIGS. 20A-20B
FIG. 20A
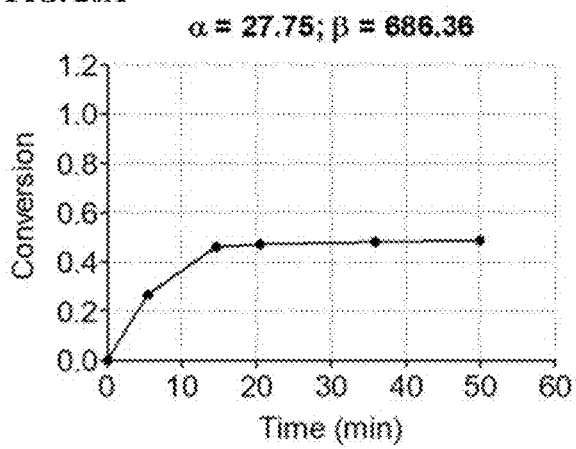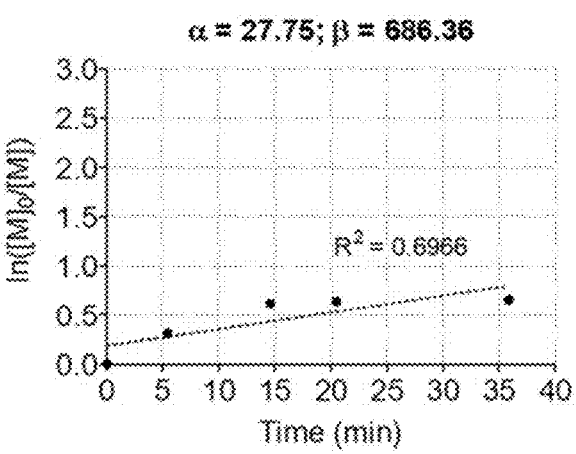
FIG. 20B
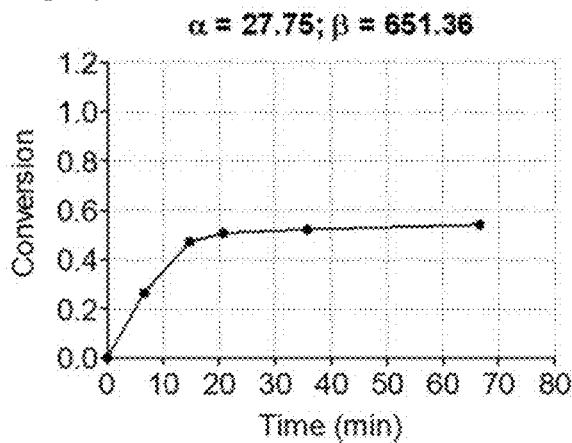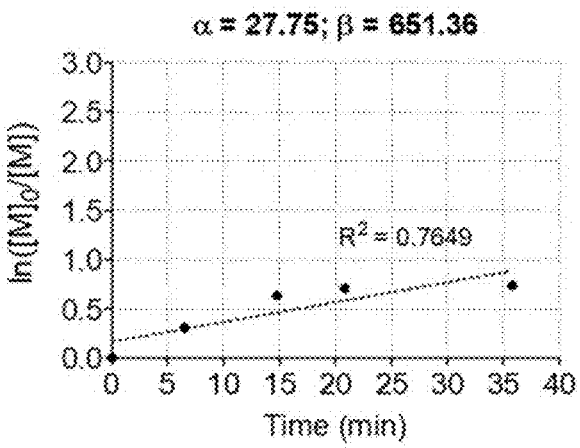

FIGS. 20C-20D
FIG. 20C
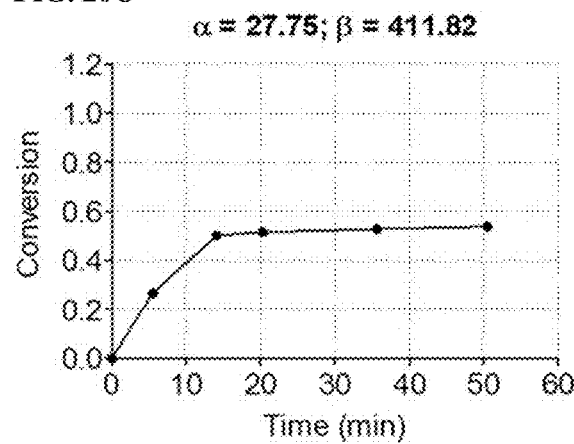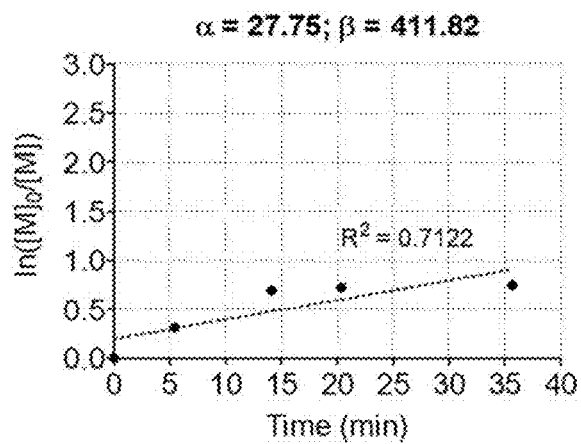
FIG. 20D
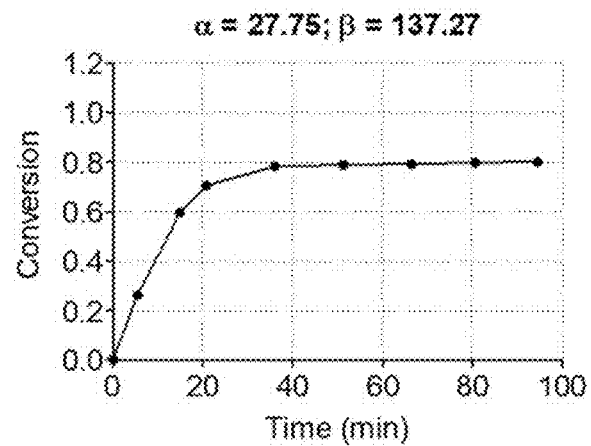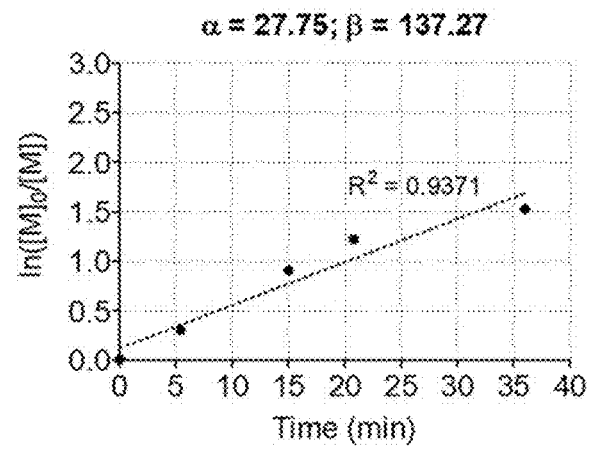

FIGS. 20E-20F
FIG. 20E
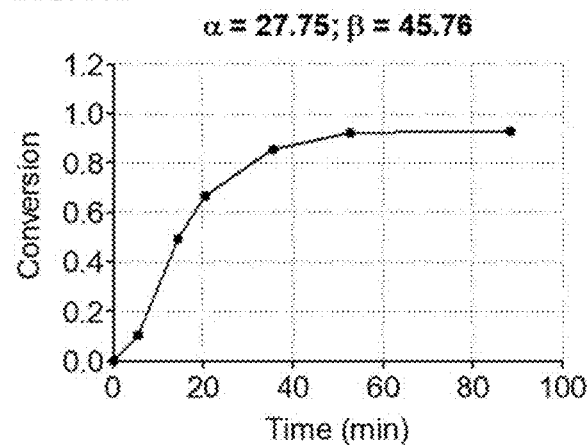
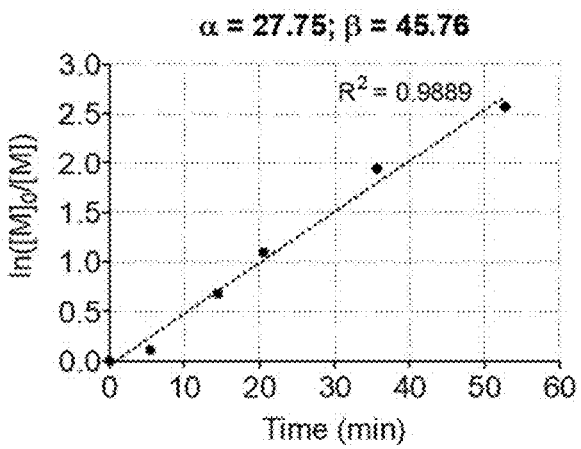
FIG. 20F
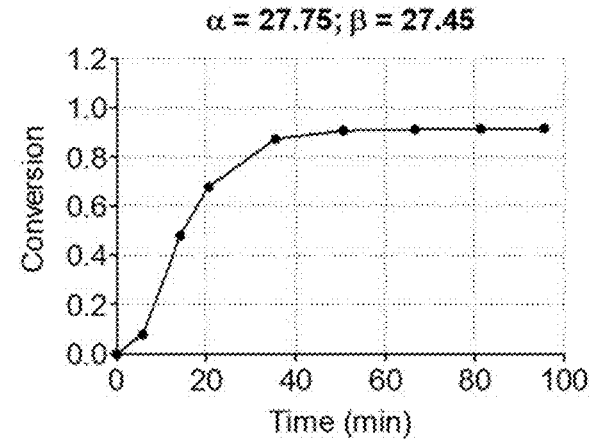
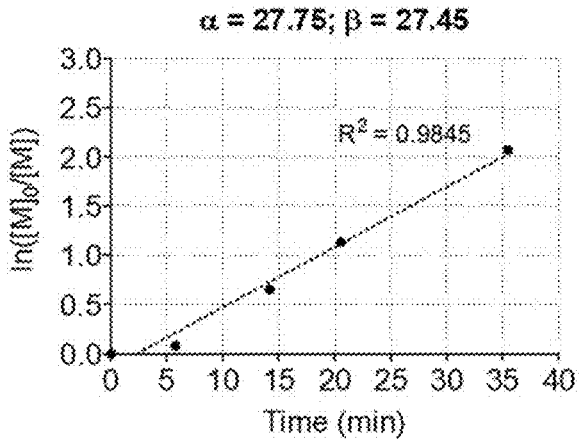

FIGS. 20G-20H
FIG. 20G
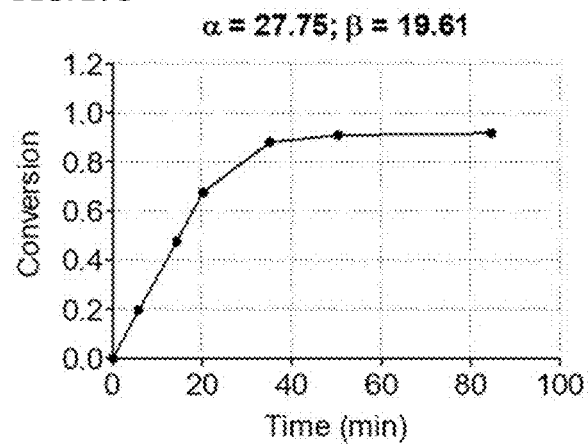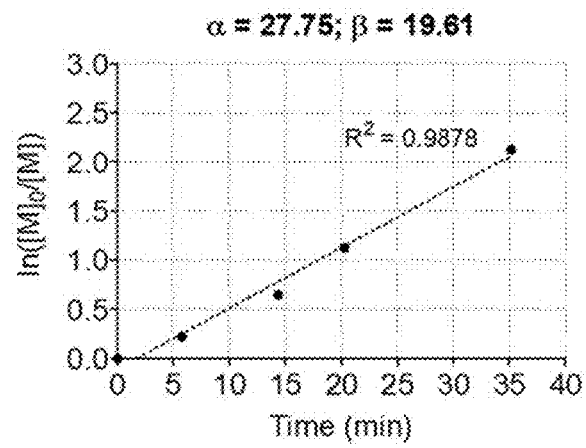
FIG. 20H
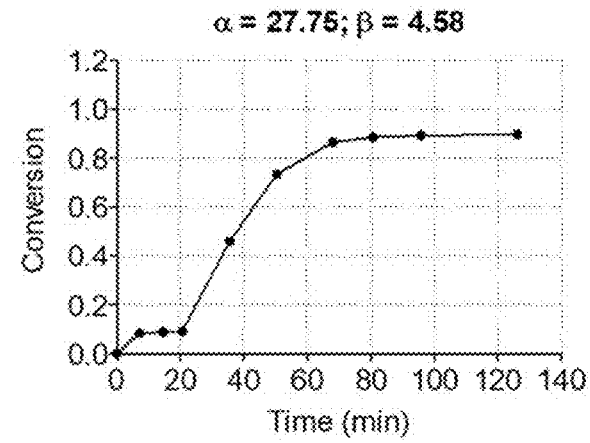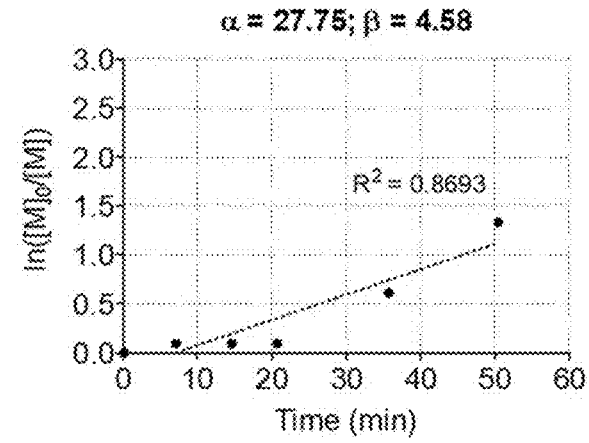

FIGS. 21A-21B
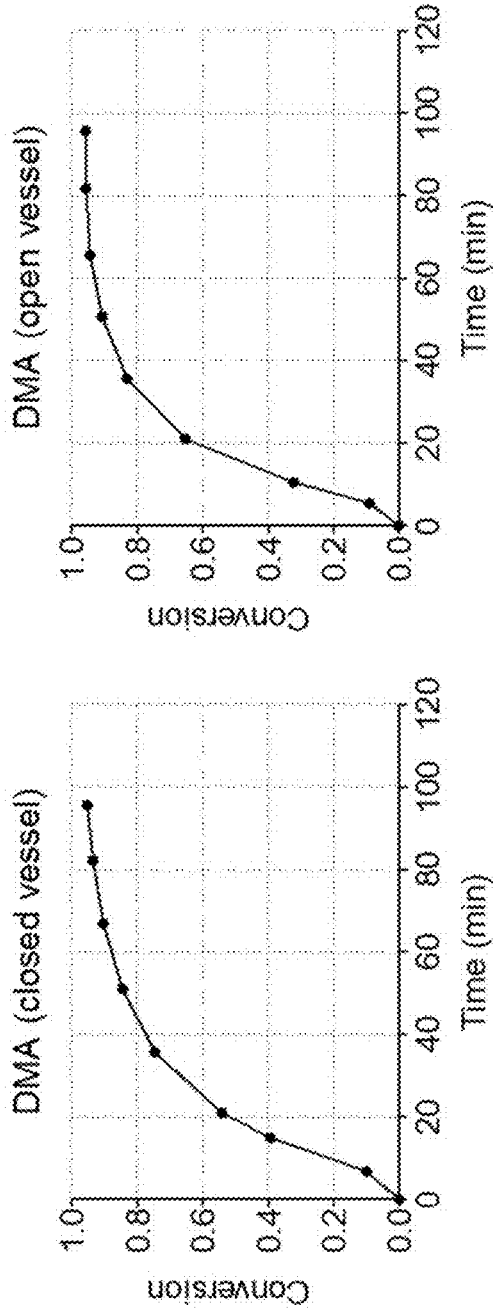
FIG. 21A
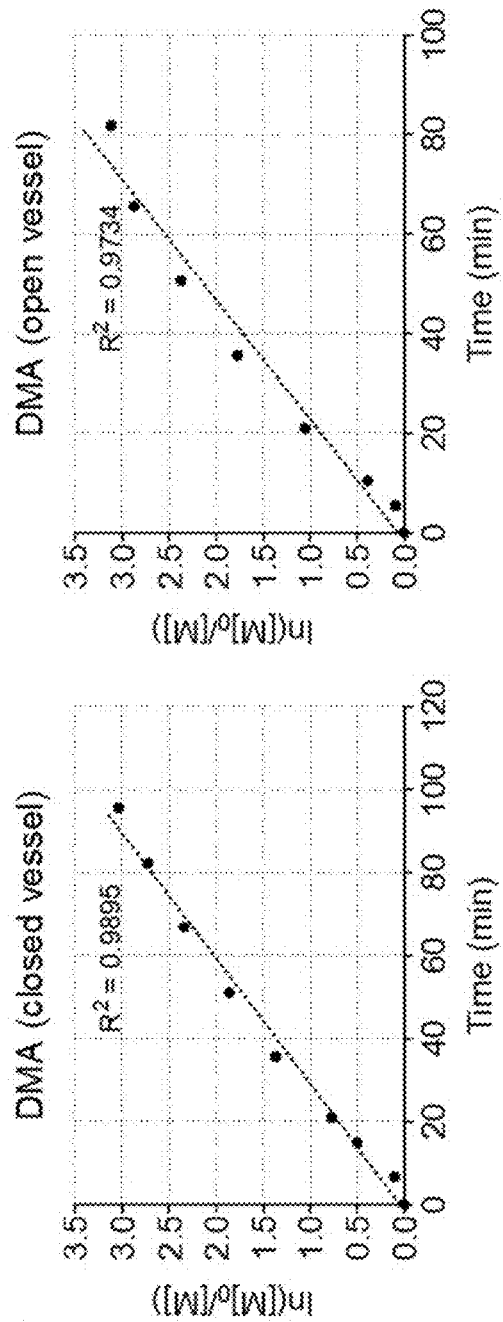
FIG. 21B

FIGS. 22A-22B
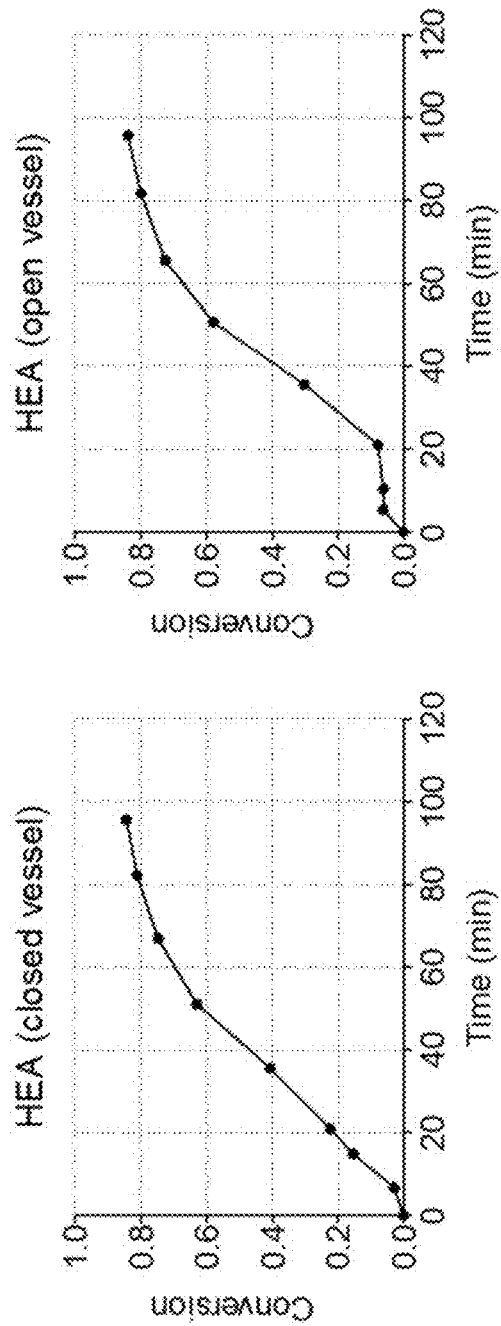
FIG. 22A
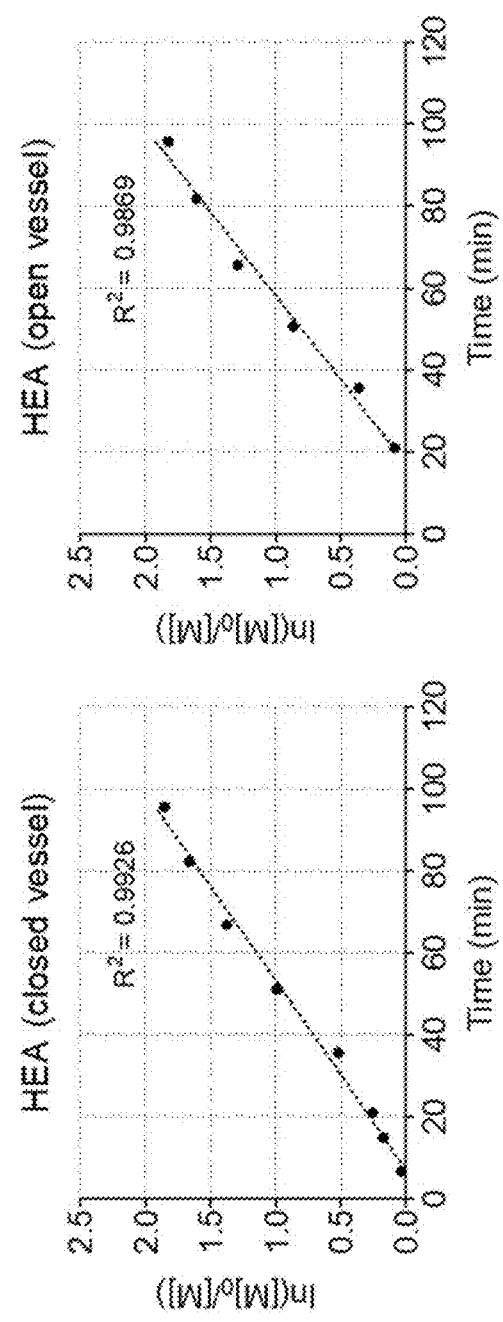
FIG. 22B

FIGS. 23A-23B
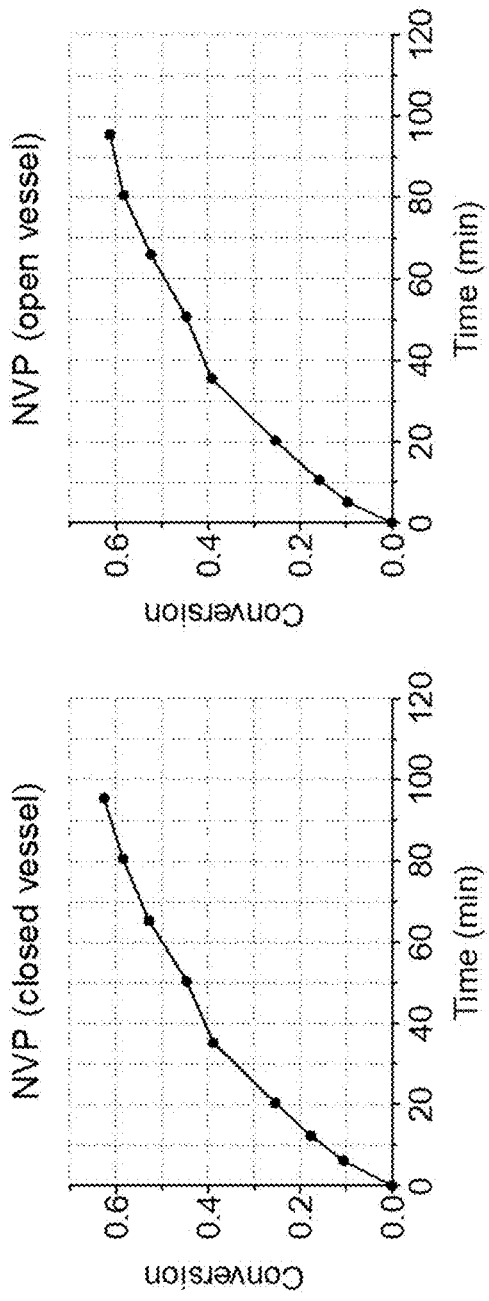
FIG. 23A
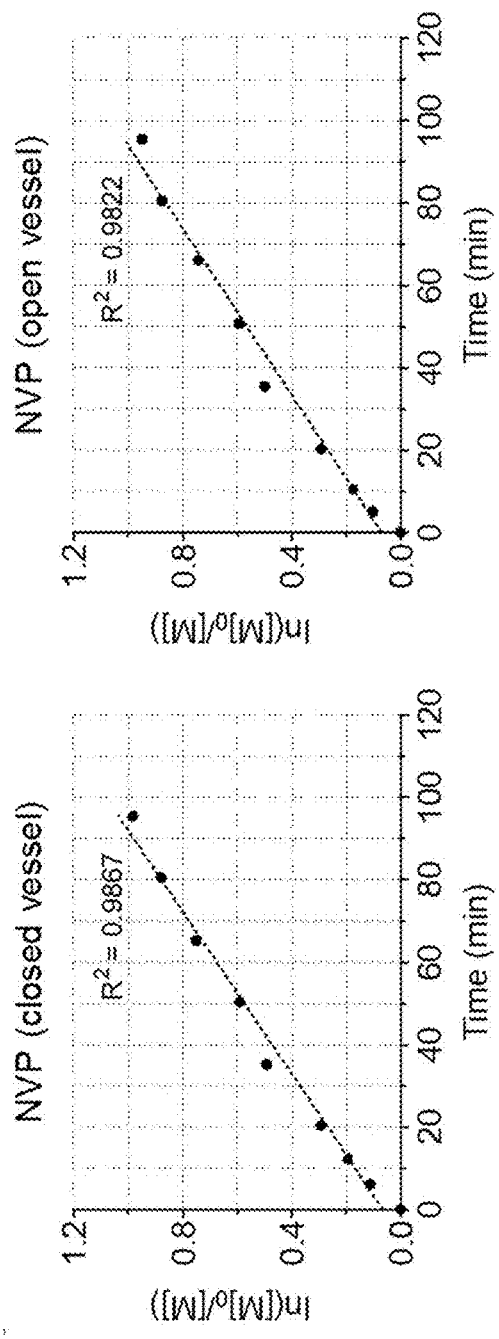
FIG. 23B

FIGS. 24A-24D
FIG. 24A
FIG. 24B
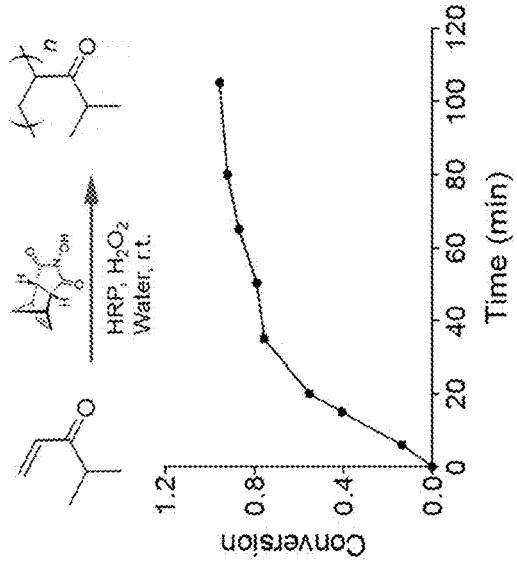
FIG. 24C
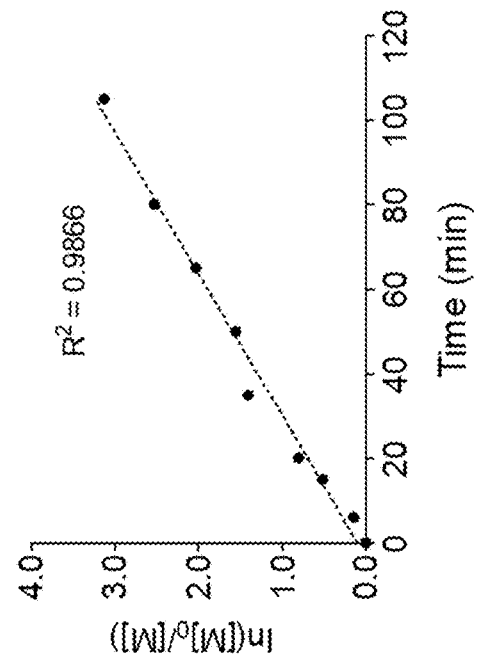
FIG. 24D
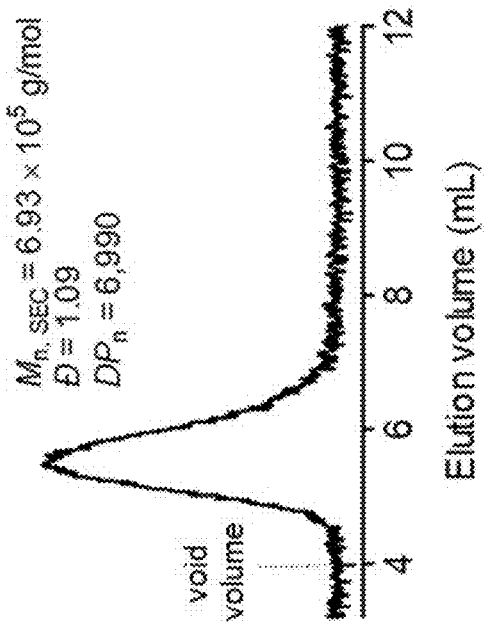

FIGS. 25A-25B
FIG. 25A
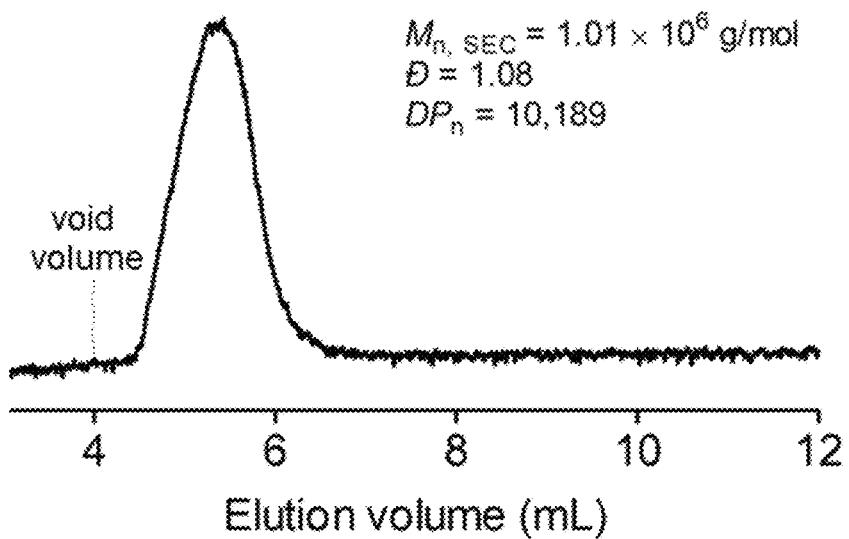
FIG. 25B
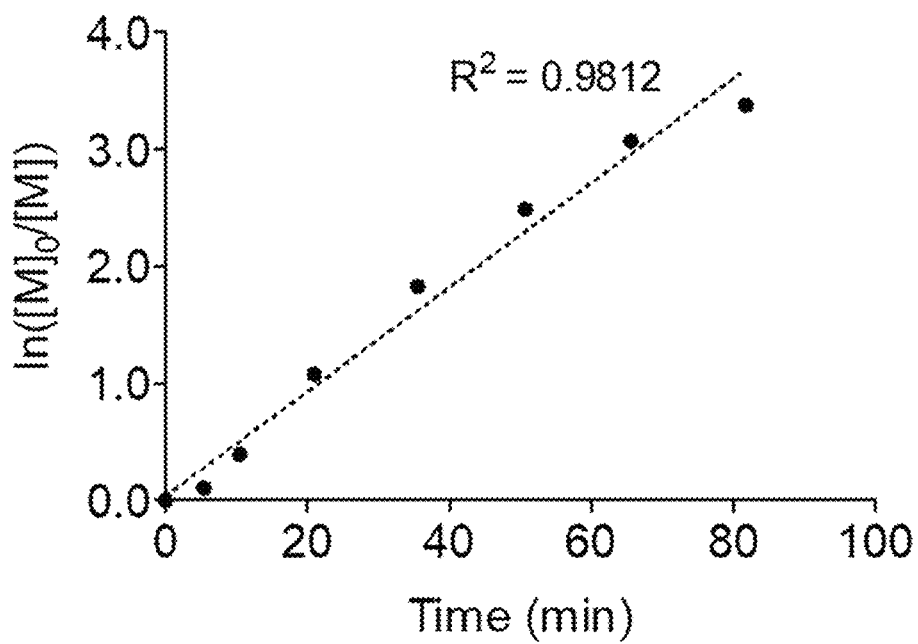

ENZYME-MEDIATED FREE RADICAL INITIATING SYSTEMS FOR THE PRODUCTION OF HYDROGELS AND CONTROLLED RADICAL POLYMERIZATION PROCESSES

CROSS-REFERENCE TO RELATED APPLICATIONS

This application claims priority to and the benefit of U.S. Provisional Patent Application No. 63/221,057, filed on Jul. 13, 2021, which is incorporated herein by reference in its entirety.

STATEMENT REGARDING FEDERALLY SPONSORED RESEARCH

This invention was made with government support under HL 157645 awarded by the National Institutes of Health. The government has certain rights in the invention.

BACKGROUND

Hydrogels are networks of cross-linked hydrophilic polymer chains capable of maintaining a three-dimensional structure while retaining large amounts of water. These gels are heavily employed in agriculture, commercial wound dressings, and hygienic products, with more recent development in biomedical applications including drug delivery, biosensing, bioimaging, and tissue engineering. Hydrogels are commonly synthesized via free radical polymerization, a method of polymerization by which the addition of active initiator species results in the formation of a polymer. Traditional radical polymerization employs heat, redox pairs, high-energy irradiation (e.g., laser, ultraviolet, infrared, X-ray, and alpha-, beta-, or gamma radiation) to generate initiating radicals, which usually requires special equipment, toxic reagents, or harsh reaction conditions that may have implications for organisms and the environment. Enzymes are indispensable substances in living cells, which catalyze various metabolic reactions to produce necessary biomacromolecules in vivo for maintaining the living system. Additionally, enzymatic catalysis is attracting increasing interest for the design and synthesis of new functional polymers in a mild, efficient, and green fashion.

Oxidoreductases (e.g., peroxidase, laccase, tyrosinase) catalyze the transfer of electrons from one molecule (e.g., an oxidant or electron receptor) to another molecule (e.g., a reductant or electron donor), leading to the generation of reactive radicals that can initiate the polymerization of vinyl monomers in water. For instance, horseradish peroxidase (HRP), an enzyme derived from horseradish root, has been employed in a wide range of environmental and biomedical applications, such as wastewater treatment, sensors, and immunoassays; it also plays an attractive role in free radical chain polymerization. A well-established radical initiating system consisting of HRP, β-diketone (e.g., acetylacetone (ACAC), 1,3-cyclopentanedione), and hydrogen peroxide ($H_2O_2$) is capable of generating a β-diketone-derived carbon-centered radical to initiate chain polymerization in aqueous media to produce polymers and three-dimensional hydrogels at room temperature (approx. 22° C.). However, an irreproducible induction period (45~360 min) may occur during the above enzymatic reaction. Additionally, β-diketones may have toxicity concerns. For instance, ACAC has relatively high toxicity (Oral; LD50=55 mg/kg rat), which may limit its potential biomedical application. It remains challenging to demonstrate an HRP-mediated initiating system without β-diketones.

In addition, the use of enzymes to catalyze free radical polymerization has attracted growing interest during the past two decades. However, conventional enzyme-mediated radical polymerization (EMRP) suffers from several drawbacks, including undesirable control of polymerization kinetics and polydispersity (Ð). These yield polymer products with unpredictable molecular weight (MW) and broad molecular weight distribution (Ð typically greater than 1.5). Reversible-deactivation radical polymerization (RDRP), also known as controlled radical polymerization (CRP), allows the synthesis of polymers with predetermined MW, narrow molecular weight distribution (i.e., Ð less than 1.5), and well-defined molecular composition. The integration of enzymatic catalysis with RDRP, i.e., enzyme-mediated reversible-deactivation radical polymerization (EM-RDRP) has gained increasing attention in recent years. RDRP techniques mainly include atom transfer radical polymerization (ATRP), reversible addition-fragmentation chain transfer (RAFT) polymerization, and nitroxide mediated polymerization (NMP). Most studies have focused on leveraging oxidoreductase (e.g., HRP, catalase, laccase) to facilitate ATRP or RAFT processes. For example, HRP has been reported to catalyze the oxidation of ACAC using $H_2O_2$ to generate ACAC-derived radicals, which can initiate well-controlled RAFT polymerization in the presence of a suitable chain-transfer agent (Zhang et al. *Macromolecules*, 2015, 48, 7792-7802). However, the application of enzyme catalysis in NMP processes has yet to be explored, possibly because NMP processes typically require high temperature (100-125° C.), which precludes the use of aqueous media needed for most of the enzyme-catalyzed reactions. Although recent studies have made it possible for the NMP process to proceed in water (Darabi et al. *Macromolecules*, 2015, 48, 72-80), the temperature required was still relatively high (75-90° C.), at which HRP will rapidly lose its enzymatic activity.

The synthesis of ultra-high-molecular-weight (UHMW; number-average molecular weight no less than $1 \times 10^6$ g $mol^{-1}$) polymers with low polydispersity has been challenging for RDRP, especially for NMP. Furthermore, RDRP processes are typically vulnerable to ambient oxygen that readily deactivates the propagating radicals and forms stabilized peroxy-radicals, inhibiting the polymerization reaction. The synthesis of UHMW polymers with RDRP in the presence of oxygen adds an additional level of challenge. To date, no study has reported the NMP process conducted in aqueous media at room temperature to afford UHMW polymers with low polydispersity.

SUMMARY

In one aspect, disclosed herein is a method for making a polymer, comprising:
(a) providing a composition comprising a vinyl monomer, N-hydroxy-5-norbornene-2,3-dicarboximide (HONB), horseradish peroxidase (HRP), and hydrogen peroxide ($H_2O_2$); and
(b) incubating the composition to provide the polymer.

In some embodiments, the composition comprises $H_2O_2$ and HRP in a molar ratio of about 5 to about 4000. In some embodiments, the composition comprises HONB and $H_2O_2$ in a molar ratio of about 1 to about 800. In some embodiments, the composition comprises HONB at a concentration of at least about 8 mM. In some embodiments, the composition comprises $H_2O_2$ at a concentration of at least about 0.2 mM.

In some embodiments, the composition further comprises an aqueous solution. In some embodiments, the aqueous solution has a pH of about 1 to about 8.

In some embodiments, step (a) comprises: (i) providing a first mixture of the vinyl monomer in an aqueous solution, and (ii) adding HONB, HRP, and $H_2O_2$ to the first mixture to provide the composition. In some embodiments, step (a) comprises: (i) providing a first mixture of HONB and $H_2O_2$, and (ii) adding HRP to the first mixture to provide the composition.

In some embodiments, the polymer is a hydrogel. In some embodiments, the vinyl monomer is selected from (meth) acrylamide monomers, (meth)acrylate monomers, N-vinyl lactam monomers, and combinations thereof. In some embodiments, the vinyl monomer is selected from acrylamide, methacrylamide, N,N-dimethyl acrylamide (DMA), N-isopropyl acrylamide (NIPAM), hydroxyethyl acrylate (HEA), poly(ethylene glycol) methyl ether acrylate (PEGA), poly(ethylene glycol) methyl ether methacrylate (PEGMA), 2-hydroxypropyl methacrylamide (HPMA), 2-hydroxyethyl methacrylate (HEMA), 2-methoxyethyl acrylate (MEA), methacrylic acid (MAA), 4-acryloylmorpholine (ACMO), dimethyl vinylphosphonate (DEVP), N-vinylcaprolactam (NVCL), N-vinyl pyrrolidone (NVP), and combinations thereof.

In some embodiments, the composition further comprises a crosslinker. In some embodiments, the crosslinker is selected from poly(ethylene glycol) diacrylate, poly(ethylene glycol) dimethacrylate, gelatin methacryloyl, acryloylated proteins, N,N'-methylene-bisacrylamide, bisphenol A glycerolate diacrylate, multi-arm acrylate-terminated poly (ethylene glycol), and combinations thereof. In some embodiments, the crosslinker is 4-arm-PEG10K-acrylate.

In some embodiments, the composition further comprises one or more water-dispersible inorganic nanomaterials. In some embodiments, the one or more water-dispersible inorganic nanomaterials are selected from gold nanoparticles, silica nanoparticles, and hydroxyapatite nanoparticles. In some embodiments, the composition further comprises gold nanoparticles having a particle size ranging from about 50 to 240 nm, silica nanoparticles having a particle size ranging from about 10 to 300 nm, or hydroxyapatite nanoparticles having a particle size ranging from about 20 to 200 nm, or any combination thereof.

In some embodiments, the method is carried out at a temperature ranging from about 15° C. to about 37° C. In some embodiments, the method is carried out in an open reaction vessel. In some embodiments, the method is carried out in a closed reaction vessel.

In another aspect, disclosed herein is an enzyme-mediated radical initiating system, wherein the system comprises N-hydroxy-5-norbornene-2,3-dicarboximide (HONB), horseradish peroxidase (HRP), and hydrogen peroxide ($H_2O_2$). In some embodiments, the system comprises $H_2O_2$ and HRP in a molar ratio of about 5 to about 4000. In some embodiments, the system comprises HONB and $H_2O_2$ in a molar ratio of about 1 to about 800. In some embodiments, the system comprises HONB at a concentration of at least about 8 mM. In some embodiments, the system comprises $H_2O_2$ at a concentration of at least about 0.2 mM. In some embodiments, system further comprises an aqueous solution. In some embodiments, the aqueous solution has a pH of about 1 to about 8.

In some embodiments, the system further comprises at least one vinyl monomer. In some embodiments, the vinyl monomer is selected from (meth)acrylamide monomers, (meth)acrylate monomers, N-vinyl lactam monomers, and combinations thereof. In some embodiments, the vinyl monomer is selected from acrylamide, methacrylamide, N,N-dimethyl acrylamide (DMA), N-isopropyl acrylamide (NIPAM), hydroxyethyl acrylate (HEA), poly(ethylene glycol) methyl ether acrylate (PEGA), poly(ethylene glycol) methyl ether methacrylate (PEGMA), 2-hydroxypropyl methacrylamide (HPMA), 2-hydroxyethyl methacrylate (HEMA), 2-methoxyethyl acrylate (MEA), methacrylic acid (MAA), 4-acryloylmorpholine (ACMO), dimethyl vinylphosphonate (DEVP), N-vinylcaprolactam (NVCL), N-vinyl pyrrolidone (NVP), and combinations thereof.

In some embodiments, the system further comprises a crosslinker. In some embodiments, the crosslinker is selected from poly(ethylene glycol) diacrylate, poly(ethylene glycol) dimethacrylate, gelatin methacryloyl, acryloylated proteins, N,N'-methylene-bisacrylamide, bisphenol A glycerolate diacrylate, multi-arm acrylate-terminated poly (ethylene glycol), and combinations thereof. In some embodiments, the crosslinker is 4-arm-PEG10K-acrylate.

In some embodiments, the system further comprises one or more water-dispersible inorganic nanomaterials. In some embodiments, the one or more water-dispersible inorganic nanomaterials are selected from gold nanoparticles, silica nanoparticles, and hydroxyapatite nanoparticles. In some embodiments, the system further comprises gold nanoparticles having a particle size ranging from about 50 to 240 nm, silica nanoparticles having a particle size ranging from about 10 to 300 nm, or hydroxyapatite nanoparticles having a particle size ranging from about 20 to 200 nm, or any combination thereof.

In another aspect, disclosed herein is a composition comprising: N-hydroxy-5-norbornene-2,3-dicarboximide (HONB), horseradish peroxidase (HRP), and hydrogen peroxide ($H_2O_2$). In some embodiments, the composition comprises $H_2O_2$ and HRP in a molar ratio of about 5 to about 4000. In some embodiments, the composition comprises HONB and $H_2O_2$ in a molar ratio of about 1 to about 800. In some embodiments, the composition comprises HONB at a concentration of at least about 8 mM. In some embodiments, the composition comprises $H_2O_2$ at a concentration of at least about 0.2 mM.

In some embodiments, the composition further comprises an aqueous solution. In some embodiments, the aqueous solution has a pH of about 1 to about 8.

In another aspect, disclosed herein is a kit comprising: N-hydroxy-5-norbornene-2,3-dicarboximide (HONB), horseradish peroxidase (HRP), and hydrogen peroxide ($H_2O_2$). In some embodiments, the kit further comprises at least one of: a container, a vinyl monomer, a crosslinker, and instructions for carrying out a polymerization reaction.

BRIEF DESCRIPTION OF THE DRAWINGS

FIGS. 5A-5D depict the gelation time determination via dynamic time sweep rheological measurement in hydrogels triggered by different ternary initiating compositions in accordance with one embodiment of the present disclosure. (FIG. 5A) [HONB]:[HRP]:[$H_2O_2$]=60.4:0.04757:1.32; (FIG. 5B) [HONB]:[HRP]:[$H_2O_2$]=60.4:0.009514:0.44; (FIG. 5C) [HONB]:[HRP]:[$H_2O_2$]=60.4:0.04757:0.44; (FIG. 5D) [HONB]:[HRP]:[$H_2O_2$]=60.4:0.009514:1.32.

FIGS. 9A-9B depict the effects of different nanoparticles on gelation time in accordance with one embodiment of the present disclosure.

FIGS. 10A-10B depicts the effects of ambient oxygen and temperature on gelation time in accordance with one embodiment of the present disclosure.

FIGS. 13A-13D show representative images of in vitro angiogenesis assay measuring the capacity of HCAECs to form networking capillary tubes in the presence of: (FIG. 13A) complete HCAEC growth medium (positive control); (FIG. 13B) PBS (negative control); (FIG. 13C) the leaching solution of A-Gel; and (FIG. 13D) the leaching solution of H-Gel, respectively, in accordance with one embodiment of the present disclosure. The angiogenic capacity of HCAECs was diminished in the presence of the leaching solution of A-Gel compared to that of H-Gel. Scale bars, 200 μm.

FIGS. 14A-14F show the: (FIG. 14A) percentage area covered by tubes, (FIG. 14B) number of total branching points, (FIG. 14C) total tube length, (FIG. 14D) the number of total loops, (FIG. 14E) number of total tubes, and (FIG. 14F) and average tube length in the positive (+) control (n=12), negative (−) control (n=10), A-Gel (n=12), and H-Gel (n=12) groups in accordance with one embodiment of the present disclosure. Quantification was performed with Wimasis image analysis software.

FIGS. 16A-16C depict the effects of the α value (i.e., [$H_2O_2$]/[HRP]) on the polymerization kinetics when keeping the β value (i.e., [HONB]/[$H_2O_2$]) at 15.25 in accordance with one embodiment of the present disclosure.

FIGS. 17A-17D depict the effects of the α value on the polymerization kinetics while keeping β=45.76 in accordance with one embodiment of the present disclosure.

FIGS. 18A-18D depict the effects of the α value on the polymerization control when keeping β=137.27 in accordance with one embodiment of the present disclosure.

FIGS. 19A-19C depict the effects of the a value on polymerization kinetics when keeping the β at a relatively low level (i.e., β=4.58) in accordance with one embodiment of the present disclosure.

FIGS. 20A-20H depict the effects of the β value on the polymerization control in accordance with one embodiment of the present disclosure.

FIGS. 21A-21B depict (FIG. 21A) monomer conversion and (FIG. 21B) kinetic plot of the polymerization of DMA in the absence (closed vessel) or presence (open vessel) of ambient oxygen in accordance with one embodiment of the present disclosure ([HONB]:[HRP]:[$H_2O_2$]=20.13:0.015857:1.32).

FIGS. 22A-22B depict (FIG. 22A) monomer conversion and (FIG. 22B) kinetic plot of the polymerization of HEA in the absence (closed vessel) or presence (open vessel) of ambient oxygen in accordance with one embodiment of the present disclosure ([HONB]:[HRP]:[$H_2O_2$]=20.13:0.015857:1.32).

FIGS. 23A-23B depict (FIG. 23A) monomer conversion and (FIG. 23B) kinetic plot of the polymerization of NVP in the absence (closed vessel) or presence (open vessel) of ambient oxygen in accordance with one embodiment of the present disclosure ([HONB]:[HRP]:[$H_2O_2$]=20.13:0.015857:1.32).

FIGS. 24A-24D show (FIG. 24A) photograph of a scaled-up, open-to-air synthesis of poly (N,N-dimethyl acrylamide) (PDMA) in accordance with one embodiment of the present disclosure under conditions: 23 mL; no headspace; no prior deoxygenation; open vessel (diameter×length, 28 mm×61 mm); no stirring; 22° C.; [DMA]=2.5 M; [HONB]:[HRP]:[$H_2O_2$]=60.40:0.047579:3.96; time: 62 h. The resulting PDMA is highly viscous, reaching 96% monomer conversion in 105 min (FIG. 24B). (FIG. 24C) The polymerization process displays near-linear pseudo-first-order kinetics. (FIG. 24D) The elution curve of the resulting PDMA obtained from size exclusion chromatography coupled to multi-angle light scattering (SEC-MALS) reveals its high degree of polymerization ($M_{n,\ SEC}$=6.93×10$^5$ g mol$^{-1}$; $DP_n$=6,990) with narrow molecular weight distribution (Ð=1.09). The void volume of this SEC-MALS system was 4 mL.

FIGS. 25A-25B show the open-to-air synthesis of ultra-high-molecular-weight (UHMW) PDMA in accordance with one embodiment of the present disclosure under conditions: 0.5 mL; no prior deoxygenation; open vessel (diameter×length, 5 mm×177.8 mm); no stirring; 22° C.; [DMA]=2.5 M; [HONB]:[HRP]:[$H_2O_2$]=20.13:0.015857:1.32; time: 72 h. (FIG. 25A) The elution curve obtained from SEC-MALS reveals the production of a UHMW PDMA ($M_{n,\ SEC}$=1.01×10$^6$ g mol$^{-1}$; $DP_n$=10,189) with narrow molecular weight distribution (Ð=1.08). The void volume of this SEC-MALS system was 4 mL. (FIG. 25B) The polymerization process displays near-linear pseudo-first-order kinetics, reaching 97% monomer conversion in 82 min.

DETAILED DESCRIPTION

Figure 1:
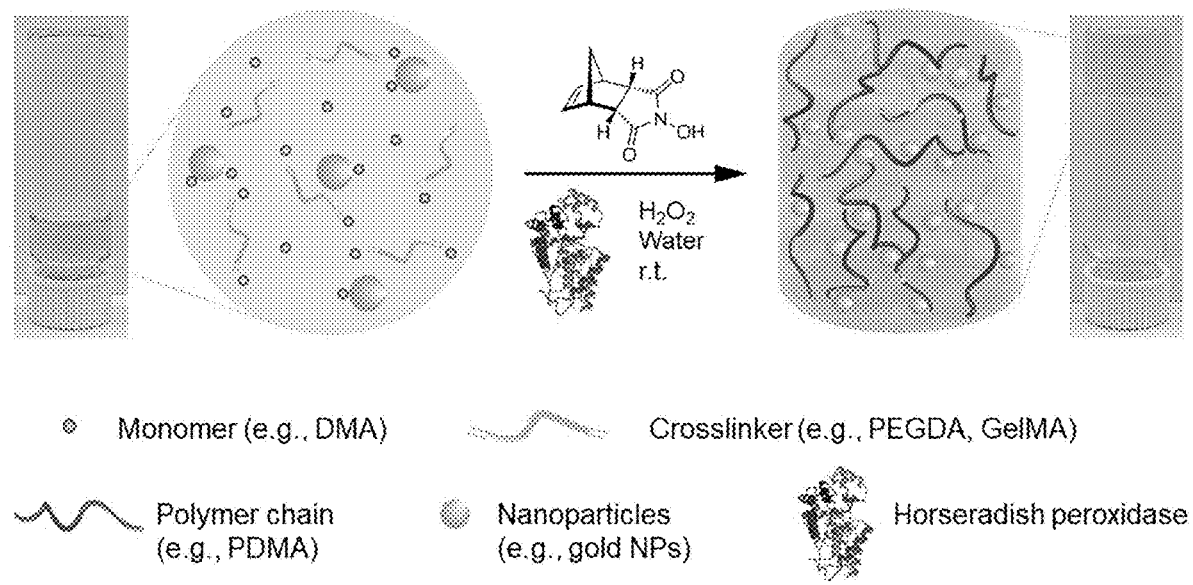
FIG. 1 shows a schematic illustration of hydrogel production via enzyme-mediated radical polymerization using the HONB-HRP-$H_2O_2$ ternary radical initiating system in accordance with one embodiment of the present disclosure.

Disclosed herein are systems, methods, and kits for conducting polymerization reactions to produce polymers, including hydrogels. In particular, disclosed herein is a ternary enzyme-mediated radical initiating system that comprises, consists of, or consists essentially of HONB, HRP, and $H_2O_2$, which can effectively initiate chain polymerization of vinyl monomers, and optionally crosslinkers, in aqueous media over a wide pH range at ambient conditions. In some embodiments, the polymerizations are well-controlled, and can produce polymers having narrow polydispersities, including ultra-high molecular weight polymers.

Previously, it had been challenging to demonstrate an HRP-mediated radical initiating system without the use of β-diketones, such as ACAC. The HONB-HRP-$H_2O_2$ ternary radical initiating system described herein presents an effective approach. Compared to prior approaches, the disclosed system and associated methods and kits provide several advantages, which include, but are not limited to, the following:

(1) A nontoxic N-hydroxyimide compound, HONB, is utilized to replace conventional β-diketones as an enzymatic substrate, which provides an HRP-mediated free radical initiation mechanism and an environmentally-friendly method to produce polymers, including hydrogels;

(2) By tuning the molar ratio of HONB, HRP, and $H_2O_2$ (e.g., the α and β values as described herein), or adjusting the pH value of the reaction medium, polymers (including hydrogels) can be produced in a mild, rapid, and facile fashion with controlled gelation times.

(3) In some embodiments, hydrogels produced with the HONB-HRP-$H_2O_2$ ternary radical initiating system display markedly higher compatibility with mammalian cells than those produced with a traditional ACAC-HRP-$H_2O_2$ initiating system;

(4) In some embodiments, the disclosed HONB-HRP-$H_2O_2$ ternary radical initiating system can be used to conduct to conduct RDRP of conjugated and unconjugated water-soluble vinyl monomers without prior deoxygenation in the absence or presence of ambient oxygen;

(5) In some embodiments, the disclosed HONB-HRP-$H_2O_2$ ternary radical initiating system can be used to conduct scaled-up (>5 g), open-to-air RDRP of water-soluble vinyl monomers without prior deoxygenation to synthesize high-molecular-weight polymers with low dispersity;

(6) In some embodiments, the disclosed HONB-HRP-$H_2O_2$ ternary radical initiating system can be used to conduct open-to-air RDRP of water-soluble vinyl monomers without prior deoxygenation to synthesize UHMW polymers with low dispersity.

1. Definitions

Articles "a" and "an" are used herein to refer to one or to more than one (i.e., at least one) of the grammatical object of the article. By way of example, "an element" means at least one element and can include more than one element.

"About" is used herein to provide flexibility to a numerical range endpoint by providing that a given value may be "slightly above" or "slightly below" the endpoint without affecting the desired result; when the term "about" is used in connection with a quantity, it is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to ±10% of the indicated number. For example, "about 10%" may indicate a range of 9% to 11%, and "about 1" may mean from 0.9-1.1. Other meanings of "about" may be apparent from the context, such as rounding off; for example, "about 1" may also mean from 0.5 to 1.4.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps and those that do not materially affect the basic and novel characteristic(s) of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitations of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

As used herein, the term "(meth)" designates optional methyl substitution. Thus, a term such as "(meth)acrylates" denotes both acrylates and methacrylates.

As used herein, the term "vinyl monomer" refers to a compound having a double bond that is capable of free radical polymerization. In some embodiments, a vinyl monomer has a group —CH=$CH_2$.

2. Enzyme-Mediated Radical Initiating System, Methods of Use Thereof, and Polymers Produced Therefore Disclosed herein is an enzyme-mediated radical initiating system, wherein the system comprises N-hydroxy-5-norbornene-2,3-dicarboximide (HONB), horseradish peroxidase (HRP, EC 1.11.1.7; 44 kDa; 301 units $mg^{-1}$), and hydrogen peroxide ($H_2O_2$). Also disclosed herein are methods of using this system to produce polymers (e.g., hydrogels), e.g., by incubating the components of the system with one or more vinyl monomers and optionally one or more crosslinkers.

Figure 2:
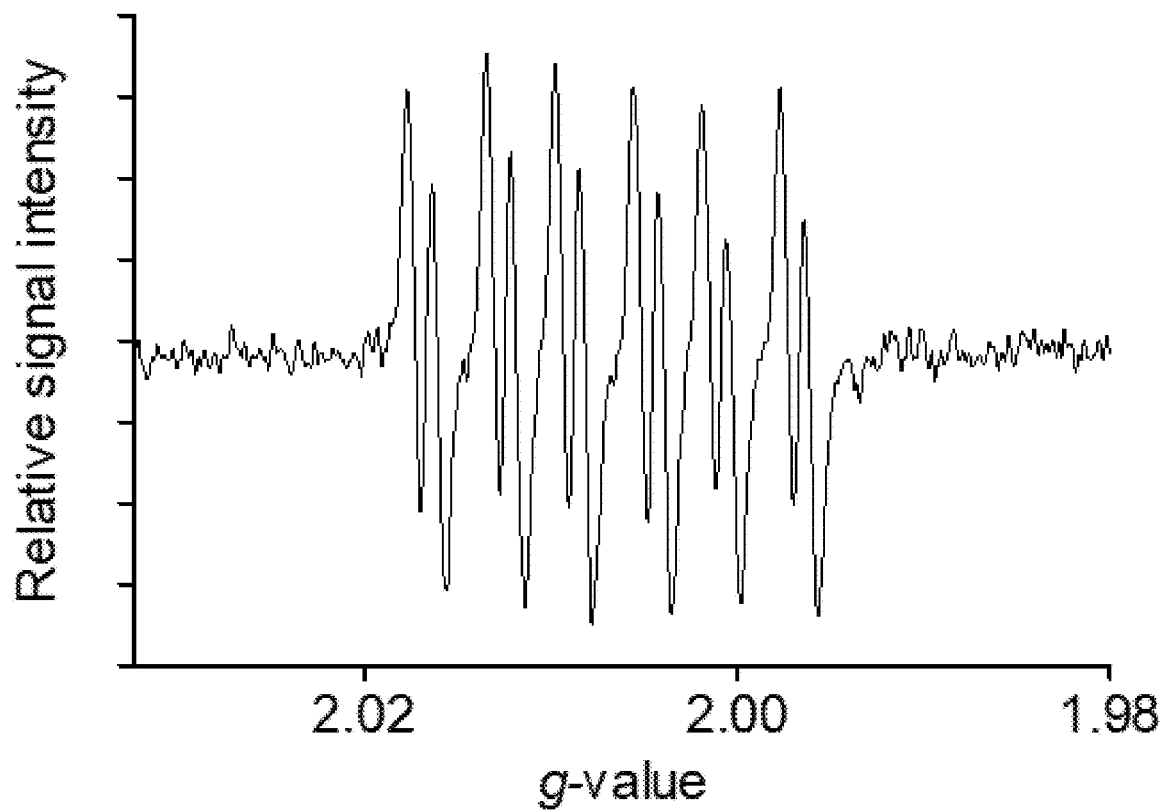
FIG. 2 depicts the electron paramagnetic resonance (EPR) spectra of the radicals formed in the HONB-HRP-$H_2O_2$ ternary system ([HONB]:[HRP]:[$H_2O_2$]=60.4:0.04757: 1.32) aqueous solution after 5 min of reaction using 5,5-dimethyl-1-pyrroline N-oxide (DMPO) as a spin trap in accordance with one embodiment of the present disclosure.
Figure 3:
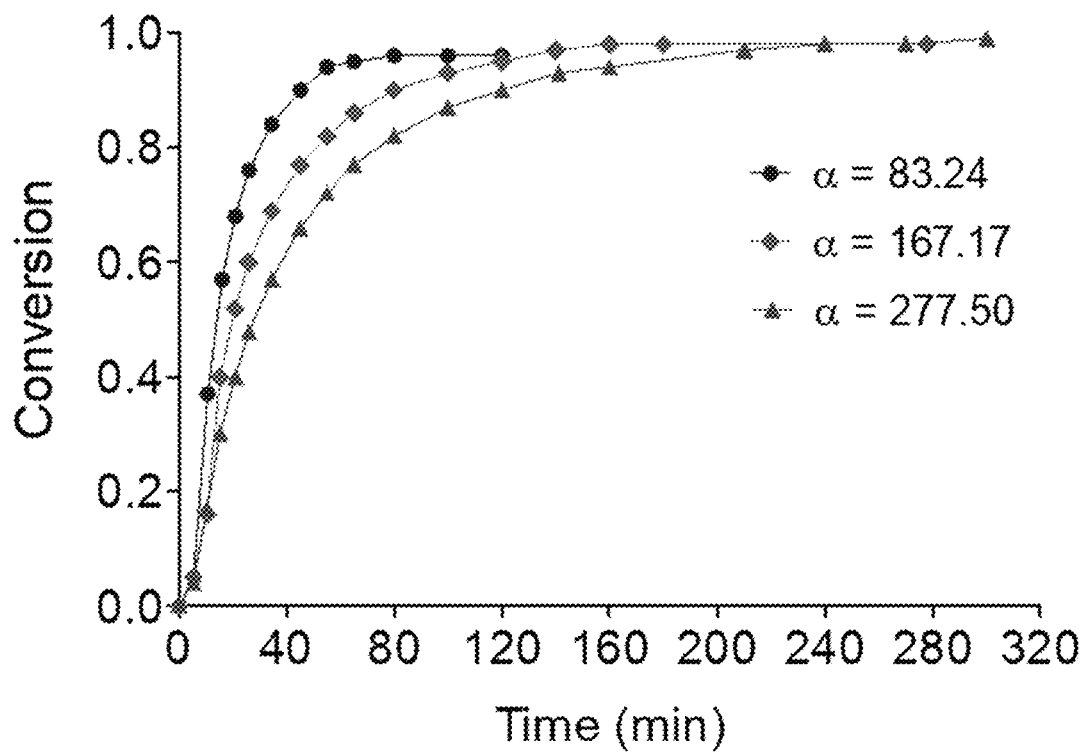
FIG. 3 shows the vinyl double bond conversion versus reaction time profiles of the polymerization of DMA at different $H_2O_2$ to HRP molar ratios (designated as a) in accordance with one embodiment of the present disclosure.

Unlike the HRP-β-diketone (e.g., ACAC)-$H_2O_2$ radical initiating system described previously, where a β-diketonederived carbon-centered radical is generated to initiate chain polymerization, the HONB-HRP-$H_2O_2$ ternary radical initiating system according to the present disclosure adopts a novel free radical initiation mechanism. According to one embodiment, electron paramagnetic resonance (EPR) analysis reveals that the initiating radical formed in the ternary system aqueous solution ([HONB]:[HRP]:[$H_2O_2$]=60.4: 0.04757:1.32) can be detected in 5 min after being adducted to 5,5-dimethyl-1-pyrroline N-oxide (DMPO) as a spin trap (see FIG. 2). The spectrum of this species shows a doublet of sextets (hyperfine coupling constants: g=2.0067, $a^N$=13.15 G, $a^H_\beta$=7.05 G, and $a^H_\gamma$=2.2 G), suggesting the formation of a nitroxide radical derived from HONB. In such embodiments, the successful initiation of radical polymerization was confirmed by the polymerization of DMA in the presence of the above ternary system with different compositions. In one embodiment, final conversion of the vinyl groups in DMA reached approx. 96~98% within 80~240 min depending on the α value, as determined by in situ nuclear magnetic resonance (NMR) analysis (see FIG. 3).

As demonstrated herein, tuning the molar ratio of HONB, HRP, and $H_2O_2$ (e.g., the α and β values as described herein) can lead to production of polymers (e.g., hydrogels) in mild and rapid fashion with controlled gelation times. For example, in some embodiments, the molar ratio of $H_2O_2$ to HRP (referred to herein as the "a value") is about 5 to about 4000, e.g., about 10 to about 2000, or about 25 to about 1000, or about 25 to about 600. In some embodiments, the molar ratio of $H_2O_2$ to HRP is about 6.94 to about 3746.25. In some embodiments, the molar ratio of $H_2O_2$ to HRP is about 27.75 to about 555. In some embodiments, the molar ratio of HONB to $H_2O_2$ (referred to herein as the "β value") is about 1 to about 800, e.g., about 2 to about 750, or about 10 to about 500, or about 15 to about 150. In some embodiments, the molar ratio of HONB to $H_2O_2$ is about 2.29 to 713.82. In some embodiments, the molar ratio of HONB to $H_2O_2$ is about 15.25 to 137.27.

In some embodiments, HONB is at a concentration of at least about 8 mM. In some embodiments, HONB is at a concentration of about 8 mM to about 300 mM. In some embodiments, $H_2O_2$ is at a concentration of at least about 0.2 mM. In some embodiments, $H_2O_2$ is at a concentration of about 0.2 mM to about 60 mM.

As shown herein, the polymerization reactions can be conducted in aqueous solution under mild conditions. In some embodiments, adjusting the pH of the solution can help tune the polymerization/gelation times. In some embodiments, the aqueous solution has a pH of about 1 to about 8. In some embodiments, the aqueous solution has a pH of about 2 to about 7. In some embodiments, the aqueous solution has a pH of about 2.3 to about 7.5.

The polymerization reactions can be conducted under ambient conditions. In some embodiments, the reaction is carried out at a temperature of about 15° C. to about 37° C., about 18° C. to about 24° C., or about 20° C. to about 24° C. In some embodiments, the reaction can be carried out at a temperature of about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., or about 37° C.

The polymerization reactions can be conducted under atmospheric conditions, i.e., in the presence of oxygen. For example, data presented herein shows that the reactions do not require any of the system components to be deoxygenated. Accordingly, in some embodiments, the polymerization reactions are conducted in an open vessel. In some embodiments, the polymerization reactions are conducted in a closed vessel, though in such embodiments, the closed vessel does not require deoxygenation. The reaction vessel can be any suitable vessel for carrying out a chemical reaction, such as a vial, a tube, a beaker, a flask, or a chemical reactor (e.g., a research reactor, a commercial reactor, an industrial reactor, or the like).

The HONB-HRP-$H_2O_2$ ternary radical initiating system can be used together in various ways when used to carry out polymerization reactions (e.g., methods disclosed herein). For example, in one embodiment the HONB and HRP can be combined first, followed by mixing with $H_2O_2$. Alternatively, according to another embodiment, the HONB and $H_2O_2$ can be combined first, followed by mixing with HRP. Yet according to another embodiment, the three components can be directly combined.

The system disclosed herein can be used to polymerize a variety of vinyl monomers, e.g., to produce polymers, including hydrogels. For example, in some embodiments, the vinyl monomer is selected from (meth)acrylates, (meth)acrylamides, N-vinyllactams, N-vinylamides, β-vinylcarbamates, β-vinylcarbonates, and the like. In some embodiments, the vinyl monomer is selected from (meth)acrylates, (meth)acrylamides, and N-vinyllactams. In some embodiments, the monomer is a water-soluble monomer, such as a water-soluble (meth)acrylate, (meth)acrylamide, N-vinyllactam, or the like. Specifically, examples thereof include, but are not limited to, acrylamide, methacrylamide, DMA, NIPAM, HEA, PEGA, PEGMA, HPMA, HEMA, MEA, MAA, ACMO, DEVP, NVCL, and NVP.

In some embodiments, one or more crosslinkers can be used in the polymerization reactions. Crosslinkers are di- or multi-functional monomers that can undergo free-radical polymerization at two or more positions on the molecule, thereby creating branch points for a polymeric material. For example, the systems and methods described herein can be used to produce hydrogels, and in such embodiments, crosslinkers can be employed. Suitable examples of radically polymerizable water-soluble crosslinkers having more than one unsaturated carbon-carbon double bond, such as di(meth)acrylates and bisacrylamides Examples include, but are not limited to, ethylene glycol di(meth)acrylate, oligoethylene glycol di(meth)acrylates (e.g., tetraethylene glycol di(meth)acrylate), poly(ethylene glycol) di(meth)acrylates, acryloylated proteins, and the like. Specific examples of crosslinkers include, but are not limited to, poly(ethylene glycol) diacrylate (PEGDA), poly(ethylene glycol) dimethacrylate (PEGDMA), gelatin methacryloyl (GelMA), methacrylated hyaluronic acid, methacrylated glycol chitosan, methacrylate-ended poly-L-lysine, alginate methacrylate, acryloylated proteins, N,N'-methylene-bisacrylamide (MBA), bisphenol A glycerolate diacrylate, and multi-arm acrylate-terminated poly(ethylene glycol) (e.g., 4-arm-PEG10K-acrylate).

In some embodiments, polymers (e.g., hydrogels) can be prepared with materials dispersed therein. For example, water-dispersible inorganic nanomaterials can be added together with the monomers and crosslinkers to produce functional nanocomposite hydrogels for potential applications in enzyme immobilization, drug delivery, and tissue engineering. Suitable examples of these nanomaterials include, but are not limited to, gold nanoparticles (AuNPs), silica nanoparticles (SNPs), and hydroxyapatite nanoparticles (nHAPs), e.g., those with particle sizes ranging from about 10 nm to about 500 nm. In one embodiment, the water-dispersible inorganic nanomaterials comprise Au NPs have a particle size range from about 50 to about 240 nm. In other embodiments, the water-dispersible inorganic nanomaterials comprise SNPs comprising a particle size range from about 10 to about 300 nm. In yet another embodiment, the water-dispersible inorganic nanomaterials comprise nHAPs comprising a particle size ranging from about 10 to about 500 nm.

The polymerization reactions can reach high yields, for example, in some embodiments, the polymerization reactions can reach up to about 90%, up to about 91%, up to about 92%, up to about 93%, up to about 94%, up to about 95%, up to about 96%, up to about 97%, up to about 98%, or up to about 99% conversion. In embodiments, the polymerization reactions can produce polymeric products with low polydispersity (Đ), which is a measure of the molecular weight distribution in a polymer sample. It is calculated using the equation $M_w/M_n$, where $M_w$ is the weight-average molecular weight and $M_n$ is the number average molecular weight. In some embodiments, the polydispersity of the polymer produced using the systems and methods disclosed herein is less than about 1.5, less than about 1.4, less than about 1.3, less than about 1.2, or less than about 1.1. In some embodiments, the polydispersity of the polymer produced using the systems and methods disclosed herein is about 1.0 to about 1.5, about 1.0 to about 1.4, about 1.0 to about 1.3, about 1.0 to about 1.2, about 1.0 to about 1.1, or about 1.5, about 1.4, about 1.3, about 1.2, or about 1.1.

Because the systems and methods disclosed herein can produce hydrogels using nontoxic HONB in place of the typically-used ACAC, the resulting hydrogels can be used in a wide variety of applications in which toxicity is a concern, particularly in wound dressings, hygienic products, and in biomedical applications including drug delivery, biosensing, bioimaging, and tissue engineering. Accordingly, also disclosed herein are methods of using hydrogels according to the methods disclosed herein, in any such applications. Also disclosed herein are polymers, e.g., hydrogels, produced using the methods disclosed herein. In some embodiments, such products have improved properties compared to materials produced using diketones such as ACAC, such as improved cytocompatibility, as demonstrated herein.

3. Kits

Kits, e.g., for use with the systems and methods described herein or in any applications described herein, are also provided. In one aspect, a kit comprises N-hydroxy-5-norbornene-2,3-dicarboximide (HONB), horseradish peroxidase (HRP), and hydrogen peroxide ($H_2O_2$). A user can use these components to conduct a polymerization reaction, e.g., to form a polymer (such as a hydrogel).

In some embodiments, the kit comprises at least two of the three components of the ternary radical initiating system disclosed herein. For example, in some embodiments, the kit comprises N-hydroxy-5-norbornene-2,3-dicarboximide (HONB) and horseradish peroxidase (HRP). In some embodiments, the kit comprises HONB and hydrogen peroxide ($H_2O_2$). In some embodiments, the kit comprises HRP and hydrogen peroxide. In each such case, the user would supply the additional component (e.g., after purchasing the component from a separate commercial source).

In some embodiments, the kit can further comprise at least one additional component. For example, a reagent can include a reconstitution buffer if the components of the crosslinkable polymers are provided as a powder. Additionally or alternatively, a reagent can include an antiseptic agent, e.g., for cleaning a wound before treatment.

In some embodiments, the kit further comprises informational material. The informational material can be descriptive, instructional, marketing or other material that relates to the systems and methods described herein and/or the use/ storage of the kit components. For example, in some embodiments, the informational material describes methods to perform a polymerization reaction.

In some embodiments, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is a link or contact information, e.g., a physical address, email address, hyperlink, website, or telephone number, where a user of the kit can obtain substantive information about the kit components and/or their use in the systems methods described herein. In some embodiments, the informational material can also be provided in any combination of formats.

In some embodiments, the kit contains separate containers, dividers, or compartments for the kit components. For example, each kit component can be contained in at least one bottle, vial, tube, or the like, and the informational material can be contained in a plastic sleeve or packet.

The following Examples are provided by way of illustration and not by way of limitation.

EXAMPLES

Example 1

1) Preparation of precursor aqueous solution: in a 7-mL glass vial, 1,339 μL of $H_2O$, 109 μL of PEGDA (MW=700; Sigma-Aldrich), and 83 μL of DMA (Alfa Aesar) were added and homogenized by vortexing.

Figure 4:
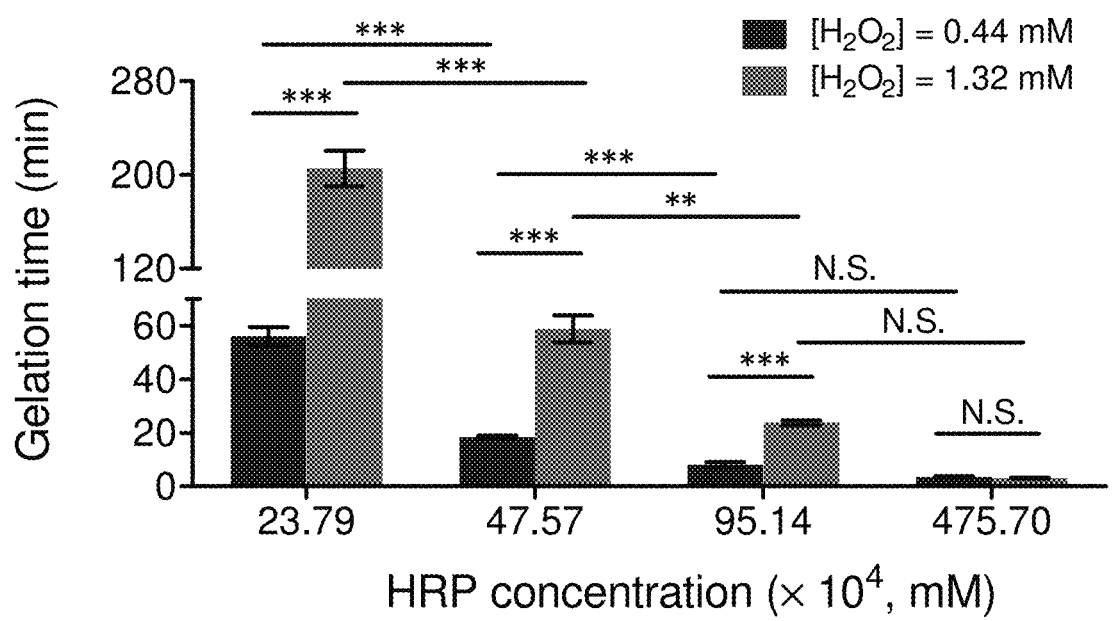
FIG. 4 depicts the effects of initial molar concentrations of HRP and $H_2O_2$ on gelation time in accordance with one embodiment of the present disclosure.

2) Hydrogel production: to the above precursor aqueous solution were added 319 μL of HONB aqueous solution (0.1208 mmol; TCI America), 100 μL of HRP aqueous solution ($9.514\times10^{-5}$ mmol; 1,260 units; Sigma-Aldrich), and 50 μL of $H_2O_2$ aqueous solution ($2.64\times10^{-3}$ mmol; Sigma-Aldrich). The glass vial was closed with a cap, followed by vortexing and letting it stand still to give a champagne pink, transparent hydrogel with a gelation time of 3.11±0.10 min (determined by a vial inversion method). While keeping the [HONB] and [$H_2O_2$] in the above precursor aqueous solution constant (i.e., 60.4 and 1.32 mM, respectively), a decrease of [HRP] from $4.757\times10^{-2}$ to $2.379\times10^{-3}$ mM (i.e., an increase in the a value from 27.75 to 555) resulted in an increase of gelation time from 3.11±0.10 to 205.36±12.38 min (see FIG. 4 and Table 1).

Figure 6:
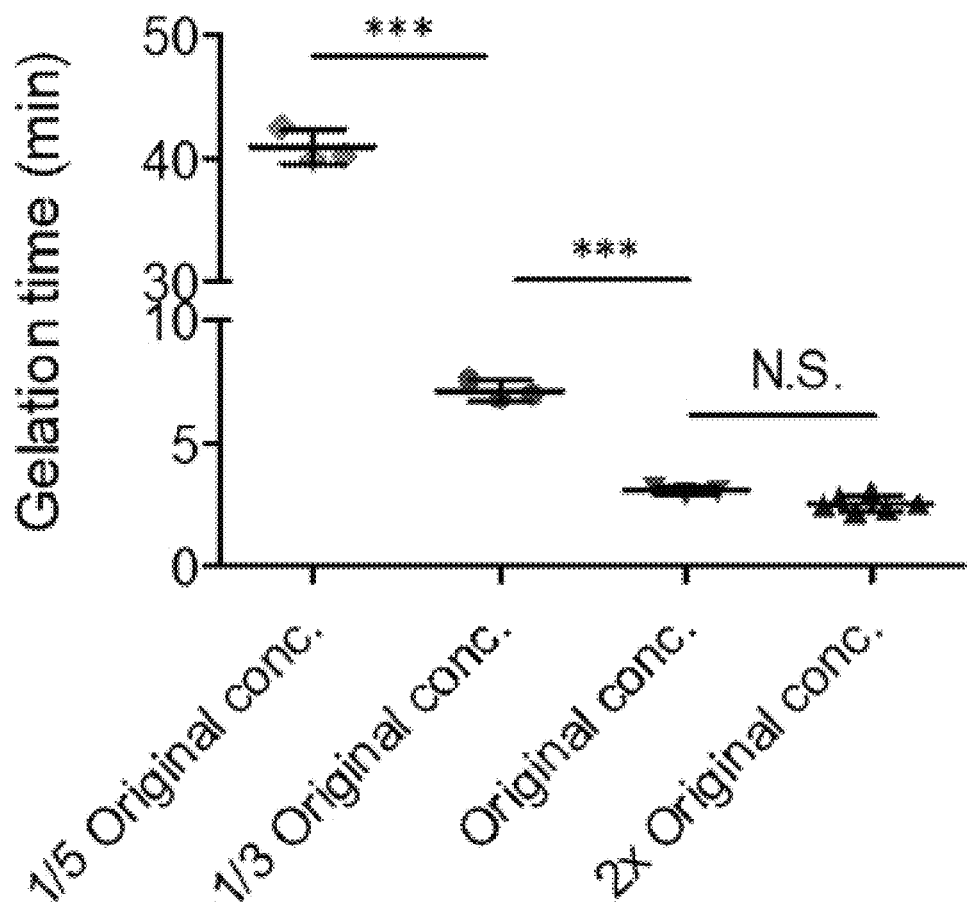
FIG. 6 shows the gelation time of the precursor aqueous solution ([PEGDA]=87.2 mM and [DMA]=402.7 mM) with increasing the overall concentration of the HONB-HRP-$H_2O_2$ ternary system from ⅕ to 2 times of the original concentration with the molar concentrations of HONB, HRP, and $H_2O_2$ being 60.4, 0.04757, 1.32 mM, respectively in accordance with one embodiment of the present disclosure.

The successful gelation was further confirmed by monitoring the storage modulus (G') and loss modulus (G") during the gelation process at room temperature using an Anton Paar MCR301 rheometer, where the time at the crossover of G' and G" is defined as the gelation time. By varying the α and β values, the gelation time could be controlled, ranging from 5.11±0.14 to 37.64±0.85 min (see FIG. 5 and Table 1). It should be noted that the volume of the headspace of air in the measurement chamber of the rheometer is different from that in the 7-ml glass vial. Therefore, the gelation times determined by rheological measurement were 1.59~1.64 times longer than those determined by the above vial inversion method. Additionally, the gelation time could be controlled by varying the overall concentration of the HRP-HONB-H$_2$O$_2$ ternary initiating system, while keeping the α and β values constant (see FIG. 6).

Example 2

Figure 7:
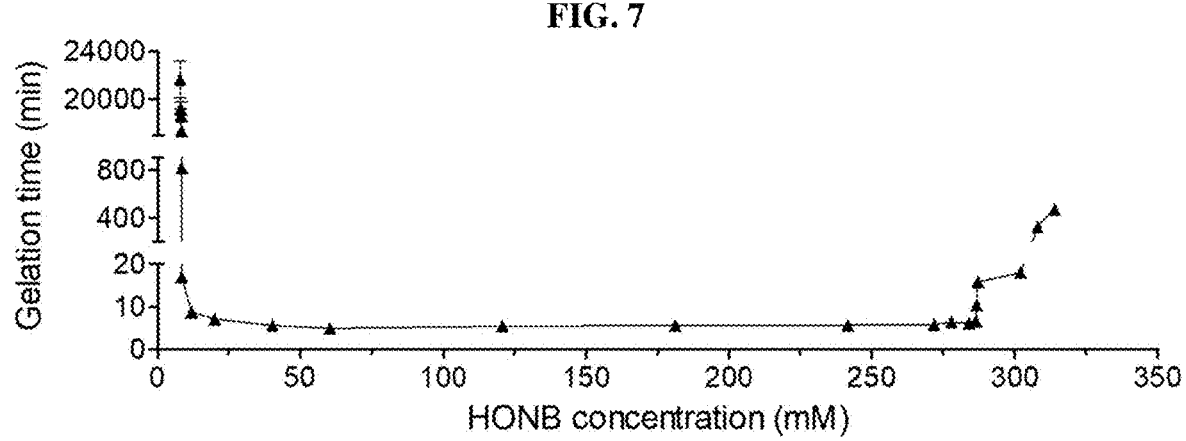
FIG. 7 depicts the effect of the molar concentration of HONB on gelation time in accordance with one embodiment of the present disclosure.
Figure 7:
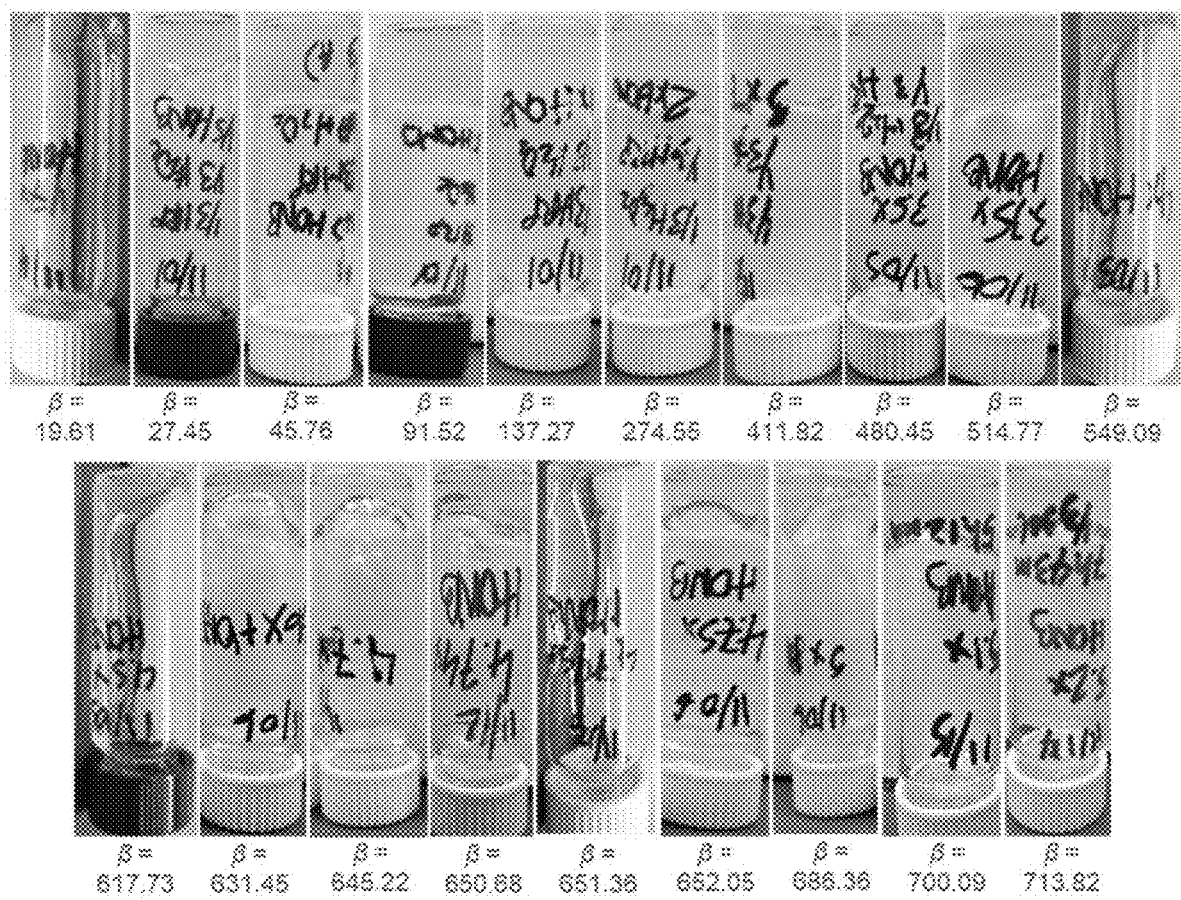

The hydrogel was produced in the same manner as described in Example 1 except that the [HONB] in the precursor aqueous solution was varied while keeping the [HRP] and [H$_2$O$_2$] constant (i.e., varying the β value while keeping α unchanged). With the increase of β from 18.30 to 137.27, the gelation time decreased from 21,656.70±1, 256.70 to 4.92±0.08 min. As the β value further increased, the gelation time increased up to 473.60±7.91 min (see FIG. 7 and Table 2). It should be noted that the increase of [HONB] in the precursor aqueous solution led to a decrease of pH value (see Table 3), however, this would not impact the gelation time as described in the following Example 3.

Example 3

1) Preparation of precursor aqueous solution: in a 50-mL tube, 5,104 μL of HONB aqueous solution (1.9321 mmol), 436 μL of PEGDA (MW=700), 332 μL of DMA, and 1,720.5 μL of H$_2$O were added and homogenized by vortexing. The pH value was then adjusted to 7.40 by adding 207.5 μL of NaOH aqueous solution (1 M).

Figure 8:
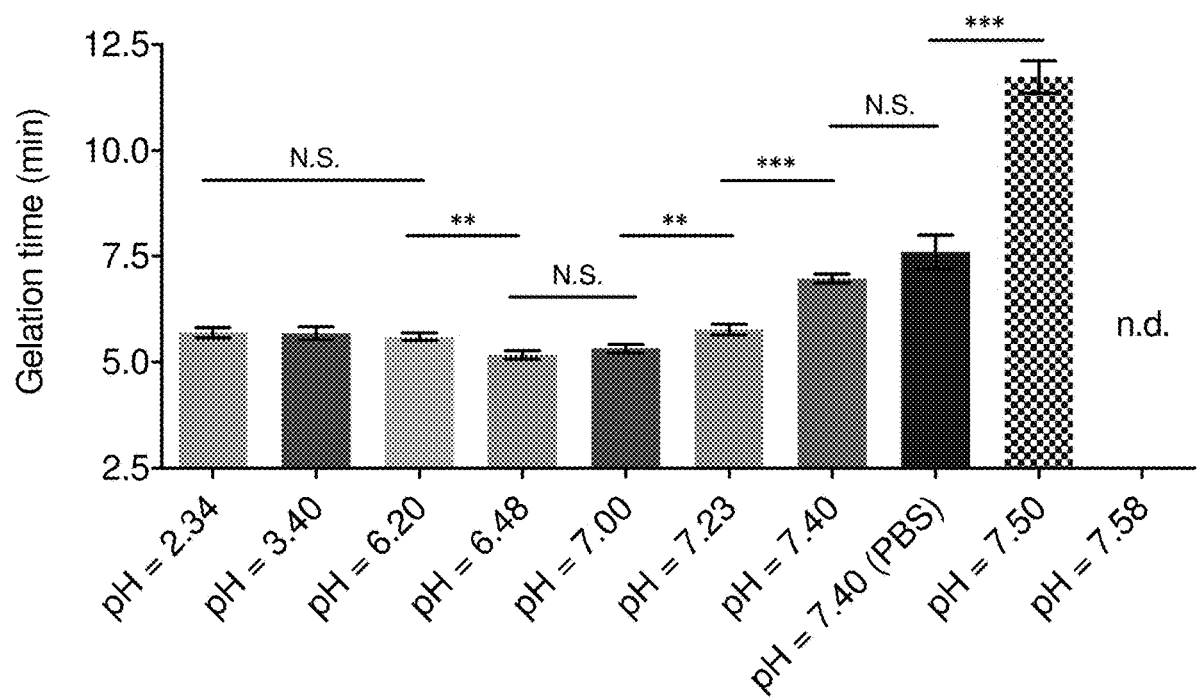
FIG. 8 depicts the effect of pH value on gelation time in accordance with one embodiment of the present disclosure.

2) Hydrogel production: to 1,950 μL of the above mixture were added 33.3 μL of HRP aqueous solution (3.1714×10$^{-5}$ mmol; 420 units), and 16.7 μL of H$_2$O$_2$ aqueous solution (8.8×10$^{-4}$ mmol). The glass vial was closed with a cap, followed by vortexing and letting it stand still at room temperature to give a hydrogel with a gelation time of 6.97±0.09 min (determined by a vial inversion method). The hydrogel was produced in the same manner as described above except that phosphate-buffered saline (PBS, 1×; Gibco) was used as the reaction medium, the gelation time was determined to be 7.59±0.33 min, which was not statistically different from that in water. By adjusting the pH value of the reaction medium with HCl (1 M) or NaOH (1 M) from 2.34 to 7.50, the gelation time could be controlled. FIG. 8 shows that the gelation time remained unchanged, regardless of the pH value changing from 2.34 to 6.20. At pH 6.48~7.0, the gelation was the fastest, possibly because the HRP shows maximal activity in this pH range. As the pH value further increased from 7.0 to 7.5, the gelation time increased from 5.32±0.08 to 11.74±0.31 min (see FIG. 8).

Example 4

1) Preparation of precursor aqueous solution: in a 7-mL glass vial, 1,105.7 μL of H$_2$O, 300 μL of gold nanoparticle aqueous solution (1.02×10$^{10}$ particles; nanoComposix), 109 μL of PEGDA (MW=700), and 83 μL of DMA were added and homogenized by vortexing.

2) Hydrogel production: to the above mixture were added 319 μL of HONB aqueous solution (0.1208 mmol), 33.3 μL of HRP aqueous solution (3.1714×10$^{-5}$ mmol; 420 units), and 50 μL of H$_2$O$_2$ aqueous solution (8.8×10$^{-4}$ mmol). The glass vial was closed with a cap, followed by vortexing and letting it stand still at room temperature to give a green, transparent nanocomposite hydrogel with a gelation time of 5.55±0.39 min (determined by a vial inversion method). Nanocomposite hydrogels were produced in the same manner as described above except that different types of nanoparticles (e.g., silica nanoparticles) with various particle sizes and concentrations were introduced. The gelation time was barely impacted by the addition of nanoparticles (see FIG. 9).

Example 5

1) Preparation of precursor aqueous solution: in a 7-mL glass vial, 1,439 μL of H$_2$O, 109 μL of PEGDA (MW=700), and 83 μL of DMA were added and homogenized by vortexing.

2) Hydrogel production: to the above mixture were added 319 μL of HONB aqueous solution (0.1208 mmol), 33.3 μL of HRP aqueous solution (3.1714×10$^{-5}$ mmol; 420 units), and 16.7 μL of H$_2$O$_2$ aqueous solution (8.8×10$^{-4}$ mmol). The glass vial was vortexed and allowed to stand still in the open air at room temperature to produce a hydrogel with a gelation time of 5.83±0.06 min (determined by a vial inversion method).

FIG. 10A shows that the hydrogel could be produced in an open vial within 6 min, although there was a significant increase in gelation time relative to its counterpart produced in a closed vial. When the temperature was elevated to 37° C., the gelation process in both the open and closed vial occurred much faster with no significant difference in gelation time. A similar gelation process with oxygen tolerance could be observed in other HRP-HONB-H$_2$O$_2$ ternary initiating formulations with various α and β values (see FIG. 10B).

Example 6

1) Preparation of precursor aqueous solution: 480 mg of GelMA (synthesized according to the protocol previously described (Su et al. ACS Appl. Mater. Interfaces, 2018, 10, 33088-33096) was dissolved in 5,480 μL of H$_2$O in a 50-mL tube at 37° C. To the above GelMA aqueous solution 400 μL of DMA, 1,276 μL of HONB aqueous solution (0.4832 mmol), and 610 μL of H$_2$O were added and homogenized by vortexing. The pH value was adjusted to 5.97 by an additional 34 μL of NaOH aqueous solution (1 M).

2) Hydrogel production: to 1,950 μL of the above mixture were added 33.3 μL of HRP aqueous solution (3.1714×10$^{-5}$ mmol; 420 units), and 16.7 μL of H$_2$O$_2$ aqueous solution (8.8×10$^{-4}$ mmol). The glass vial was closed with a cap, vortexed, and then allowed to stand still in a 37° C. ventilated oven to give a hydrogel with a gelation time of 2.97±0.05 min (determined by a vial inversion method).

Example 7

1) Preparation of precursor aqueous solution: in a 7-mL glass vial, 1,436 μL of H$_2$O, 86 μL of NVP, 109 μL of PEGDA (MW=700) were added and homogenized by vortexing.

2) Hydrogel production: to the above precursor aqueous solution were added 319 μL of HONB aqueous solution (0.1208 mmol), 33.3 μL of HRP aqueous solution (3.1714×10$^{-5}$ mmol; 420 units), and 16.7 μL of H$_2$O$_2$ aqueous solution (8.8×10$^{-4}$ mmol). The glass vial was closed with a cap, followed by vortexing and letting it stand still at room temperature to give a hydrogel with a gelation time of 2.38±0.13 min (determined by a vial inversion method).

Example 8

1) Preparation of precursor aqueous solution: in a 2-mL glass vial, 1,339 μL of H$_2$O, 109 μL of PEGDMA (MW=750; Sigma-Aldrich), and 83 μL of DMA were added and homogenized by vortexing.

2) Hydrogel production: to the above precursor aqueous solution were added 319 μL of HONB aqueous solution (0.1208 mmol), 100 μL of HRP aqueous solution (9.514× $10^{-5}$ mmol; 1,260 units), and 50 μL of $H_2O_2$ aqueous solution (2.64×$10^{-3}$ mmol). The glass vial was closed with a cap, vortexed, and then allowed to stand still in a 37° C. ventilated oven to give a hydrogel with a gelation time of 18.70±0.69 min (determined by a vial inversion method).

Example 9

1) Preparation of precursor aqueous solution: in a 7-mL glass vial, 1,339 μL of $H_2O$, 83 μL of NVP, 109 μL of PEGDA (MW=700) were added and homogenized by vortexing.

2) Hydrogel production: to the above precursor aqueous solution were added 319 μL of HONB aqueous solution (0.1208 mmol), 100 μL of HRP aqueous solution (9.514× $10^{-5}$ mmol; 1,260 units), and 50 μL of $H_2O_2$ aqueous solution (2.64×$10^{-3}$ mmol). The glass vial was closed with a cap, followed by vortexing and letting it stand still at room temperature to give a hydrogel with a gelation time of 0.97±0.04 min (determined by a vial inversion method).

Example 10

1) Preparation of precursor aqueous solution: in a 7-mL glass vial, 870 μL of $H_2O$, 109 μL of PEGDA (MW=700), and 83 μL of DMA were added and homogenized by vortexing.

2) Hydrogel production: to the above precursor aqueous solution were added 638 μL of HONB aqueous solution (0.2416 mmol), 200 μL of HRP aqueous solution (1.9028× $10^{-4}$ mmol; 2,520 units), and 100 μL of $H_2O_2$ aqueous solution (5.28×$10^{-3}$ mmol). The glass vial was closed with a cap, followed by vortexing and letting it stand still to give a hydrogel with a gelation time of 2.58±0.27 min (determined by a vial inversion method).

Example 11

1) Preparation of precursor aqueous solution: in a 7-mL glass vial, 931 μL of $H_2O$, 100 μL of NVP, and 500 μL of 4-arm-PEG10K-acrylate aqueous stock solution (MW=10,000; 8.09×$10^{-3}$ mmol) were added and homogenized by vortexing.

2) Hydrogel production: to the above precursor aqueous solution were added 319 μL of HONB aqueous solution (0.1208 mmol), 100 μL of HRP aqueous solution (9.514× $10^{-5}$ mmol; 1,260 units), and 50 μL of $H_2O_2$ aqueous solution (2.64×$10^{-3}$ mmol). The glass vial was closed with a cap, followed by vortexing and letting it stand still at room temperature to give a hydrogel with a gelation time of 1.93±0.05 min (determined by a vial inversion method).

Example 12

1) Preparation of precursor aqueous solution: in a 7-mL glass vial, 931 μL of $H_2O$, 100 μL of NVP, and 500 μL of 4-arm-PEG10K-acrylate aqueous stock solution (MW=10,000; 8.09×$10^{-3}$ mmol) were added and homogenized by vortexing.

2) Production of hydrogel and its leaching solution: to the above precursor aqueous solution were added 319 μL of HONB aqueous solution (0.1208 mmol), 100 μL of HRP aqueous solution (9.514×$10^{-5}$ mmol; 1,260 units), and 50 μL of $H_2O_2$ aqueous solution (2.64×$10^{-3}$ mmol). The glass vial was closed with a cap, followed by vortexing and letting it stand still at room temperature to give a hydrogel in 2 min. After being retrieved from the glass vial, the hydrogel was rinsed trice with PBS and minced into small pieces. 500 mg of hydrogel particles (approx. 500 μm in diameter) were incubated in 1 mL of complete H9c2 cell growth medium or HCAEC growth medium for 48 h at 4° C. to produce a leaching solution (designated as H-Gel). The above leaching solution underwent sterile filtering through a 0.22 μm filter to ensure the elimination of pathogens before its cellular response assessment.

3) Production of hydrogel with the traditional ACAC-HRP-$H_2O_2$ initiating system and its leaching solution: The hydrogel was produced according to the protocol previously described with minor modification (Su et al. *Chem. Commun.*, 2013, 49, 8033-8035). Briefly, 100 μL of NVP, and 500 μL of 4-arm-PEG10K-acrylate stock solution (MW=10,000; 8.09×$10^{-3}$ mmol), and 1,164.3 μL of $H_2O$ were introduced into a 7-mL glass vial and homogenized by vortexing to give a precursor aqueous solution.

To the above precursor aqueous solution were added 12.3 μL of ACAC (0.12 mmol; Sigma-Aldrich), 173.4 μL of HRP aqueous solution (1.65×$10^{-4}$ mmol; 2,185.2 units), and 50 μL of $H_2O_2$ aqueous solution (4.62×$10^{-2}$ mmol). The glass vial was closed with a cap, followed by vortexing and letting it stand still at room temperature to give a hydrogel in 20 min. After being retrieved from the glass vial, the above hydrogel was rinsed trice with PBS and minced into small pieces. 500 mg of hydrogel particles (approx. 500 μm in diameter) were incubated in 1 mL of complete H9c2 cell growth medium or HCAEC growth medium for 48 h at 4° C. to produce a leaching solution (designated as A-Gel). The above leaching solution underwent sterile filtering through a 0.22-μm filter to ensure the elimination of pathogens before its cellular response assessment.

4) Cell viability and proliferation assay: The H9c2 cardiomyoblasts derived from embryonic rat heart were obtained from American Type Culture Collection (ATCC CRL-1446) and expanded in the high-glucose Dulbecco's modified Eagle's medium (Thermo Fisher Scientific), supplemented with 10% fetal bovine serum (Thermo Fisher Scientific), GlutaMAX supplement (1×; Thermo Fisher Scientific), and 50 μg/mL gentamicin (Thermo Fisher Scientific). The H9c2 cells were used at passages 21-23. The HCAECs (Lonza CC-2585) were expanded in the complete growth media consisting of an EBM-2 basal medium (Lonza CC-3156) and EGM-2 MV microvascular endothelial cell growth medium supplements (Lonza CC-4147) and used at passages 6-8.

Figure 11:
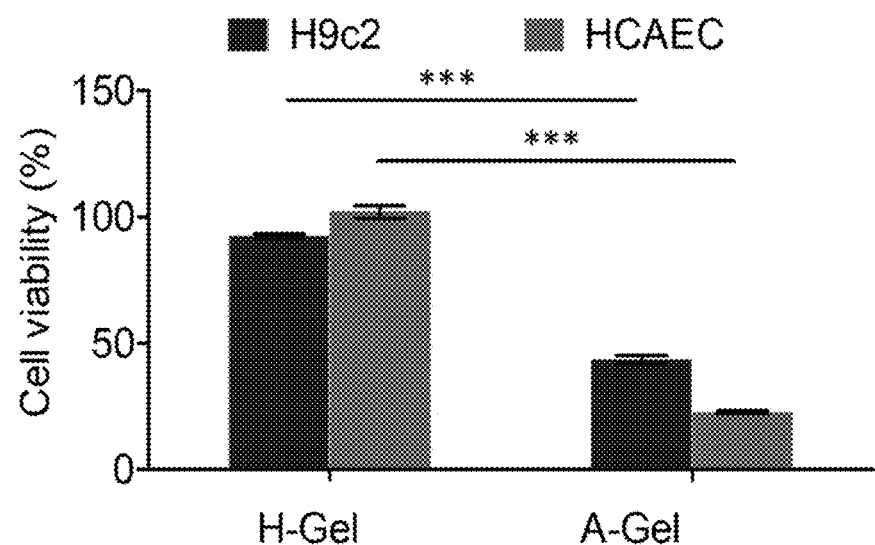
FIG. 11 depicts the viability of H9c2 cardiomyoblasts and human coronary artery endothelial cells (HCAECs) in the presence of the leaching solutions of H-Gel and A-Gel, respectively, measured using CCK-8 assays after 48 h incubation (37° C., 5% $CO_2$) in accordance with one embodiment of the present disclosure.
Figure 12:
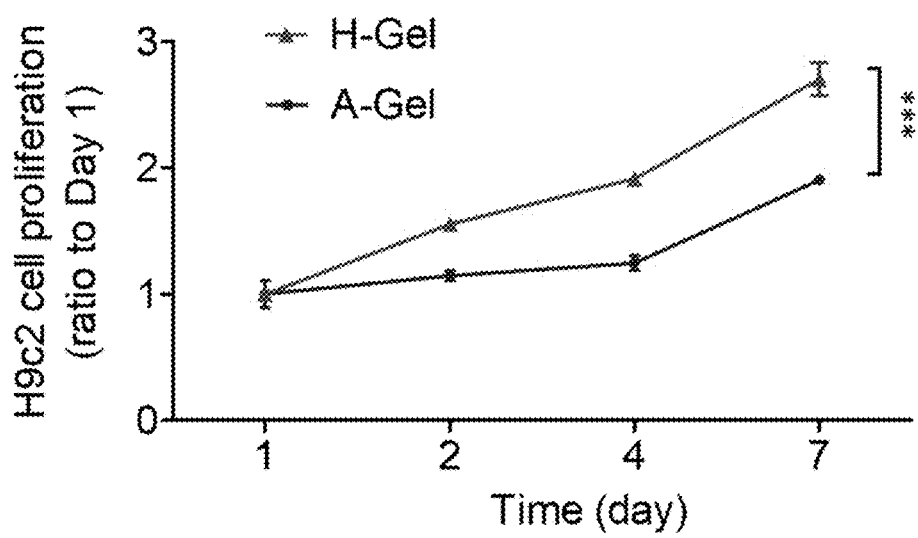
FIG. 12 shows the proliferation of H9c2 cardiomyoblasts over time in the presence of the leaching solutions of different hydrogels in accordance with one embodiment of the present disclosure.
Figure 13A:
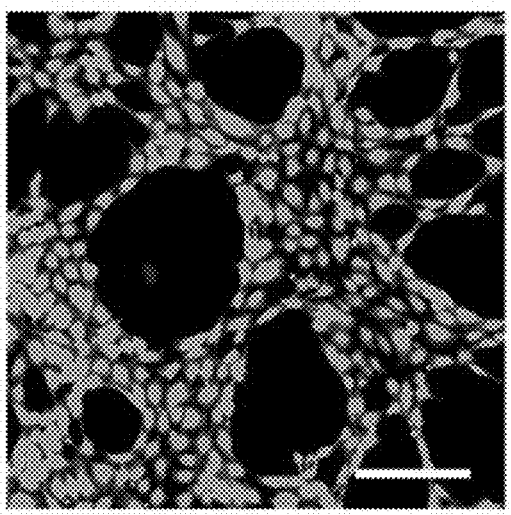
Figure 13B:
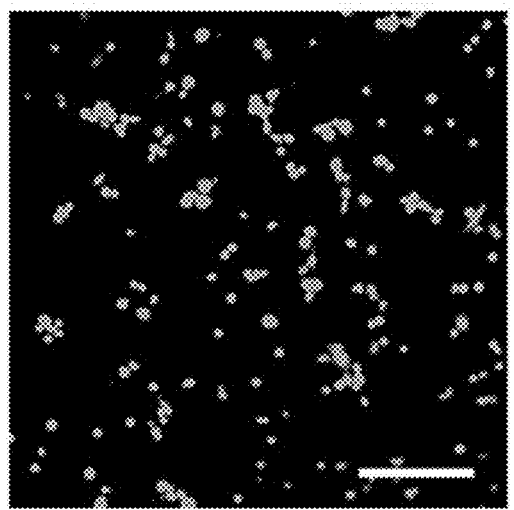
Figure 13C:
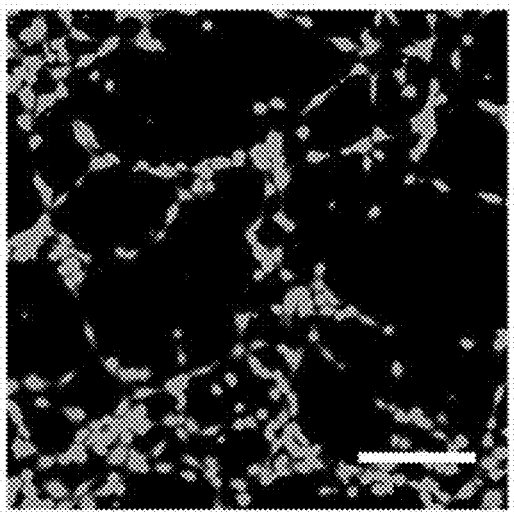
Figure 13D:
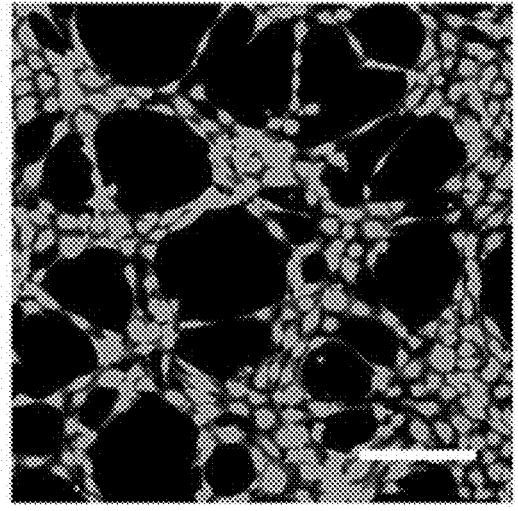

For determining the cytotoxicity of the above H-Gel and A-Gel leaching solutions, different cells were seeded at 10,000 cells per well in 96-well plates and cultured in the presence of H-Gel or A-Gel leaching solution at 37° C., 5% $CO_2$ for 48 h. Afterward, the viability of different cells was determined using a Cell Counting Kit-8 (CCK-8; Dojindo) according to the manufacturer's instructions. For assessing the proliferation potential of H9c2 cardiomyoblasts, the cells were seeded at 5,000 cells per well in 96-well plates and cultured in the presence of H-Gel or A-Gel leaching solution at 37° C., 5% $CO_2$. The metabolic activities of cultured cells at different time intervals were determined using a CCK-8 assay as described above. The leaching solution of hydrogels prepared with the HONB-HRP-$H_2O_2$ radical initiating system (i.e., H-Gel) exhibits excellent compatibility with mammalian cells, including H9c2 cardiomyoblasts and HCAECs with high (>92%) cellular viability after 48 hr of incubation. Additionally, the above leaching solution supports the growth of H9c2 cardiomyoblasts over one week. In contrast, the leaching solution of hydrogels prepared from the traditional ACAC-HRP-$H_2O_2$ initiating system (i.e., A-Gel) is toxic to both types of cells and significantly impairs the proliferative potential of H9c2 cardiomyoblasts (see FIGS. 11 and 12).

5) In-vitro angiogenesis assay: HCAECs were plated onto the polymerized Cultrex basement membrane extract with reduced growth factor (R&D Systems) at 10,000 cells per well in the presence of complete HCAEC growth medium (positive control), PBS (negative control), H-Gel or A-Gel leaching solution in the μ-Slide angiogenesis micro-wells (ibidi GmbH). After 5 h, tube formation was imaged from 10-12 random fields in different treatment groups using a Zeiss LSM 880 confocal laser scanning microscope. The percentage of area covered by tubular structures, total branching points, total tube length, average tube length, and the numbers of total loops and tubes were quantified with Wimasis image analysis software. The H-Gel leaching solution promoted the tube formation of HCAECs comparable to the positive control, while the angiogenic capacity of HCAECs was diminished in the presence of the A-Gel leaching solution (see FIGS. 13 and 14).

Example 13

Closed-vessel polymerization of DMA without prior deoxygenation in NMR tubes: 103.05 μL of DMA (1.000 mmol), 10.65 μL of 1,4-Dioxane (0.125 mmol; Sigma-Aldrich), and 601.86 μL of D20 were homogenized by vortexing. After the successive addition of 159.48 μL of HONB aqueous solution in D20 (0.0604 mmol), 49.96 μL of HRP aqueous solution in D20 ($4.758 \times 10^{-5}$ mmol; 630 units), and 75 μL of $H_2O_2$ aqueous solution in D20 ($3.96 \times 10^{-3}$ mmol), the time counting began while 0.5 mL of the above reaction mixture was immediately transferred into a capped NMR tube as the reaction vessel (diameter×length, 5 mm×177.8 mm; SP Wilmad-LabGlass) and placed into the probe of NMR spectrometer for analysis. The time-dependent $^1$H NMR spectra of the sample were collected in situ at pre-determined time intervals using a Bruker Topspin program on a Bruker Avance Neo 500 MHz multinuclear NMR spectrometer at 22° C. 1,4-Dioxane was used as an internal standard to calculate the conversion of vinyl double bonds, as its single peak at 3.75 ppm separates from the signals of other chemicals in the reaction system. All chemical reagents were used without prior deoxygenation.

Figure 15:
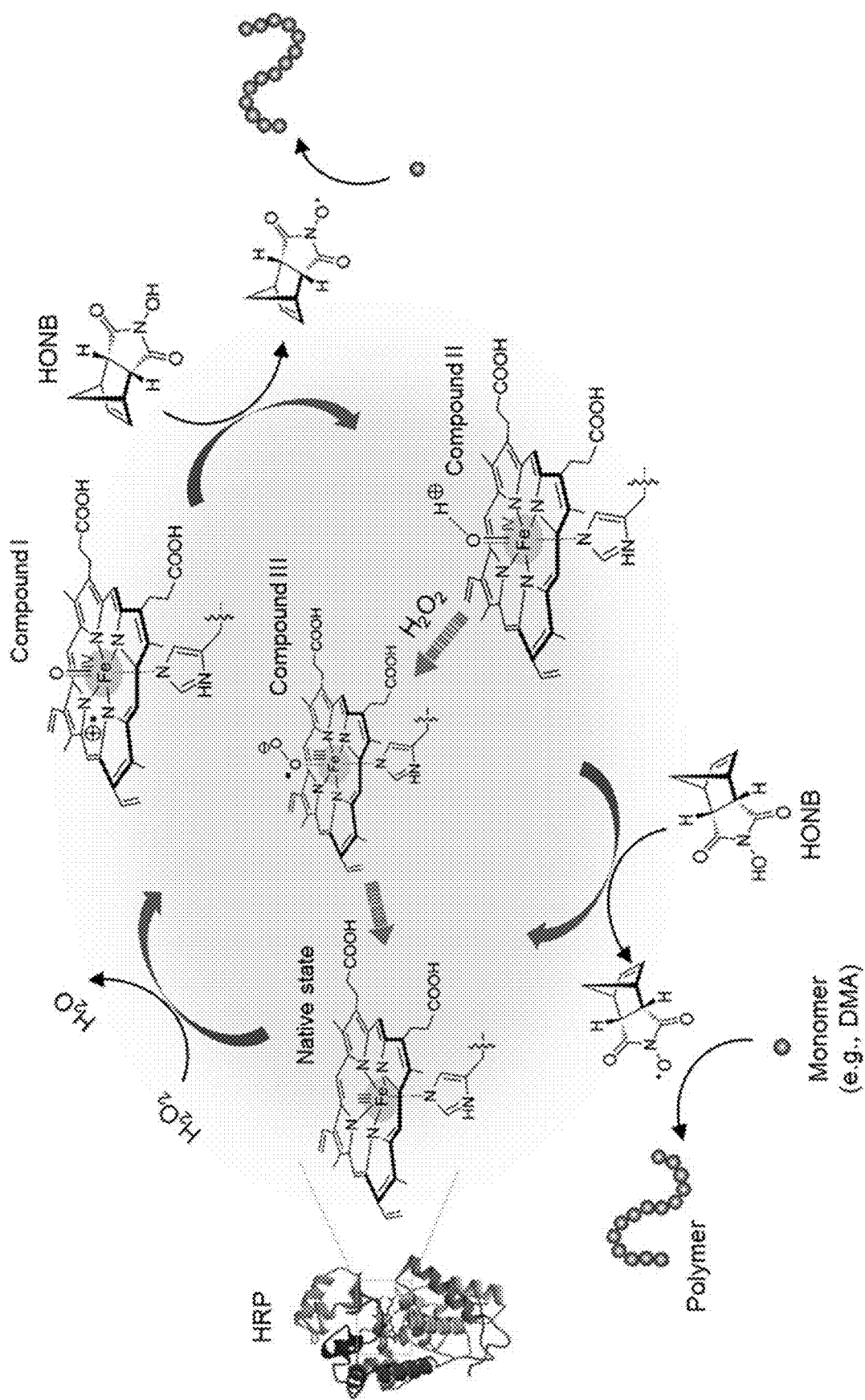
FIG. 15 shows a proposed mechanism of HRP-mediated generation of HONB-derived nitroxide radicals to initiate polymerization of vinyl monomers in accordance with one embodiment of the present disclosure.

The polymerization of DMA was readily initiated by the HONB-HRP-$H_2O_2$ ternary system. FIG. 15 shows a proposed mechanism of HRP-mediated generation of HONB-derived nitroxide radicals to initiate polymerization. Near-linear pseudo-first-order kinetics, which is characteristic of an RDRP process, were observed, indicating a constant radical concentration during the polymerization process to produce PDMA with monomer conversion up to 98% in 106 min (see FIG. 16A). Increasing the α value from 83.24 to 277.50 while maintaining the β value at 15.25 resulted in a decrease in reaction rate; however, this exerted little impact on the near-linear pseudo-first-order kinetics (see FIG. 16). A similar trend with an increase in α value was observed when maintaining (β=45.76 (see FIG. 17). $H_2O_2$ is a known substrate of HRP; however, it can also inactivate the enzyme at high concentrations. In the HONB-HRP-$H_2O_2$ ternary system, both $H_2O_2$ and HONB serve as the substrates for HRP. As the α value increases, the increase in $H_2O_2$ concentration could inhibit the enzymatic activity, leading to a reduced concentration of initiating radicals in the reaction system and a decrease in polymerization rate.

Furthermore, when maintaining (3 at a relatively high value (i.e., (3=137.27), increasing the α value also slowed down the polymerization rate. Interestingly, this process was accompanied by an improved polymerization control (see FIGS. 18 C and D). This phenomenon could possibly be explained by that the reduced concentration of initiating radicals may facilitate establishing a delicate activation-deactivation equilibrium between the propagating (macro) radicals and the dormant radicals trapped by the HONB-derived nitroxides in the system, thereby leading to a more constant propagating radical concentration and a better linear evolution of ln[1/(1−conversion)] with time.[22]

The impact of the α value on polymerization kinetics was further investigated while keeping β at a relatively low level (i.e., (β=4.58). FIG. 19 shows that as the α value increased, the polymerization was retarded, consistent with the previous results. However, in contrast to the situation where (β=137.27, the lowered polymerization rate was associated with a significant inhibition (>80 min) and deterioration of polymerization control. The HONB-derived nitroxide initiating radicals are supposed to promote the propagation of the polymer chain. In the reaction systems with a low β value, according to the proposed catalytic mechanism of the HONB-HRP-$H_2O_2$ ternary system, the inadequate HONB concentration can induce the inactivation of HRP by $H_2O_2$ in the initial stage, which is detrimental to the polymerization process. Therefore, increasing the α value resulted in a long inhibition period up to approx. 160 min and with minimal polymerization (see FIGS. 19 B and C).

The β value also significantly impacts the polymerization control. FIG. 20 shows that when increasing the β value from 19.61 to 45.76 while keeping α constant (i.e., α=27.75), the polymerization of DMA displayed near-linear pseudo-first-order kinetics, as expected for a controlled radical polymerization (see FIG. 20 E-G). The polymerization process was rapid, with over 92% conversion achieved within 90 min. A lowered concentration of HONB (β<19.61) decreased the polymerization reaction rate. Interestingly, increasing the β value above 45.76 also impeded the polymerization of DMA, accompanied by a significant reduction of monomer conversion (e.g., lower than 50% as shown in FIG. 20A) and deterioration of polymerization control (see FIG. 20A-D). Therefore, HONB has a competitive role in the polymerization process, acting as both a necessary substrate to generate the initiating radicals and an inhibitor at high concentrations, corroborated by the results denoted in FIG. 7 and Table 2.

Example 14

Open-to-air polymerization of DMA without prior deoxygenation in NMR tubes: 103.05 μL of DMA (1.000 mmol), 10.65 μL of 1,4-Dioxane (0.125 mmol), and 791.51 μL of D20 were homogenized by vortexing. After the successive addition of 53.15 μL of HONB aqueous solution in D20 (0.02013 mmol), 16.65 μL of HRP aqueous solution in D20 ($1.5857 \times 10^{-5}$ mmol; 210 units), and 25 μL of $H_2O_2$ aqueous solution in D20 ($1.32 \times 10^{-3}$ mmol), the time counting began while 0.5 mL of the above reaction mixture was immediately transferred into an uncapped NMR tube and placed into the probe of NMR spectrometer for analysis as described in Example 13. All chemical reagents were used without prior deoxygenation.

FIG. 21 shows that the polymerization of DMA initiated by the HONB-HRP-$H_2O_2$ system in open-ended NMR tubes is insensitive to the ambient oxygen, displaying near-linear pseudo-first-order kinetics and high monomer conversion (>95%) in 96 min, similar to those obtained in closed-ended NMR tubes.

Furthermore, the RDRP initiated by the HONB-HRP-$H_2O_2$ system can be extended to the polymerization of other conjugated and unconjugated water-soluble vinyl monomers as described below. Specifically, examples of conjugated monomers thereof include, but are not limited to, (meth) acrylamide, NIPAM, HEA, PEGA, and PEGMA. Specifically, examples of unconjugated monomers thereof include, but not limited to NVP. Open-to-air polymerization of HEA initiated by the HONB-HRP-$H_2O_2$ system without prior deoxygenation in NMR tubes exhibited near-linear pseudo-first-order kinetics and high monomer conversion up to 84% within 96 min, comparable to those polymerized in closed NMR tubes (see FIG. 22). Furthermore, polymerization of NVP initiated by the HONB-HRP-$H_2O_2$ system without prior deoxygenation in NMR tubes also exhibited near-linear pseudo-first-order kinetics, regardless of the presence of ambient oxygen, with reasonable monomer conversion (>60%) achieved within 96 min (see FIG. 23).

Example 15

Open-to-air polymerization of DMA without prior deoxygenation in 1-mL glass vials: 103.05 μL of DMA (1.000 mmol) and 612.51 μL of D20 were homogenized by vortexing. After the successive addition of 159.48 μL of HONB aqueous solution in D20 (0.0604 mmol), 49.96 μL of HRP aqueous solution in D20 ($4.758 \times 10^{-5}$ mmol; 630 units), and 75 μL of $H_2O_2$ aqueous solution in D20 ($3.96 \times 10^{-3}$ mmol), the time counting began while 0.495 mL of the above reaction mixture was immediately transferred into an uncapped 1-mL glass vial as the reaction vessel (diameter×length, 8 mm×35 mm; Thermo Fisher Scientific), followed by letting it stand still at room temperature to conduct polymerization in the presence of ambient oxygen. All chemical reagents were used without prior deoxygenation. The reaction mixture was quenched by 2,6-di-tert-butyl-4-methylphenol (BHT; Thermo Fisher Scientific), followed by mixing with 2,2,3,3-d4-3-(trimethylsilyl) propionic acid sodium salt (TMSP-d4; Sigma-Aldrich) as an internal standard for NMR analysis. The open-vessel polymerization of DMA initiated by the above HONB-HRP-$H_2O_2$ system in a 1-mL glass vial displayed near-linear pseudo-first-order kinetics and achieved a high monomer conversion of 95.6% in 105 min.

Example 16

Scaled-up, open-to-air polymerization of DMA without prior deoxygenation: 5,925.49 μL of DMA (57.5 mmol) and 10,532.39 μL of D20 were homogenized by vortexing and transferred into a 20-mL glass vial as the reaction vessel with no headspace (diameter×length, 28 mm×61 mm; DWK Life Sciences). After the successive addition of 3,668.04 μL of HONB aqueous solution in D20 (1.389 mmol), 1,149.08 μL of HRP aqueous solution in D20 ($1.093 \times 10^{-3}$ mmol; 14,478.4 units), and 1,725 μL of $H_2O_2$ aqueous solution in D20 ($9.108 \times 10^{-2}$ mmol), the time counting began. The glass vial was uncapped and allowed to stand still at room temperature to conduct polymerization in the presence of ambient oxygen. All chemical reagents were used without prior deoxygenation. Samples were withdrawn at predetermined time intervals and quenched with the addition of BHT, followed by mixing with TMSP-d4 as an internal standard for NMR analysis. After 62 h of polymerization, the PDMA product was collected and purified via extensive dialysis again deionized water (MWCO: 1 kDa), followed by lyophilization for SEC-MALS analysis. The scaled-up, open-to-air polymerization of DMA initiated by the above HONB-HRP-$H_2O_2$ system in an uncapped 20-mL glass vial displayed near-linear pseudo-first-order kinetics and achieved a high monomer conversion of 95% in 105 min. The resulting PDMA product was a white solid in excellent yield (no less than 92%), with a high molecular weight ($M_{n, SEC}=6.93 \times 10^5$ g $mol^{-1}$; $DP_n=6,990$) and low dispersity (Đ=1.09) confirmed by SEC-MALS analysis (see FIG. 24).

Example 17

Open-to-air polymerization of DMA for the synthesis of UHMW polymers was conducted under conditions as follows: [HONB]:[HRP]:[$H_2O_2$]=20.13:0.015857:1.32; [DMA]=2.5 M; no prior deoxygenation; room temperature. 257.63 μL of DMA (2.500 mmol) and 647.57 μL of D20 were homogenized by vortexing. After the successive addition of 53.15 μL of HONB aqueous solution in D20 (0.02013 mmol), 16.65 μL of HRP aqueous solution in D20 ($1.586 \times 10^{-5}$ mmol; 210 units), and 25 μL of $H_2O_2$ aqueous solution in D20 ($1.32 \times 10^{-3}$ mmol), the time counting began while 0.5 mL of the above reaction mixture was immediately transferred into an open-ended NMR tube as the reaction vessel (diameter×length, 5 mm×177.8 mm; SP Wilmad-LabGlass), followed by letting it stand still at room temperature to conduct polymerization. All chemical reagents were used without prior deoxygenation. All chemical reagents were used without prior deoxygenation. After 72 h of polymerization, the PDMA product was collected and purified via extensive dialysis again deionized water (MWCO: 1 kDa), followed by lyophilization to give a white solid. The open-to-air polymerization of DMA initiated by the above HONB-HRP-$H_2O_2$ system displayed near-linear pseudo-first-order kinetics, reaching 97% monomer conversion in 82 min, and produced a UHMW PDMA ($M_{n, SEC}=1.01 \times 10^6$ g $mol^{-1}$; $DP_n=10,189$) with low dispersity (Đ=1.08) (see FIG. 25).

TABLE 1

Effects of the initial concentrations of HONB, $H_2O_2$, and HRP on gelation time [a]

| Entry | [HONB] (mM) | [$H_2O_2$] (mM) | [HRP] × $10^4$ (mM) | $\alpha$ [b] | $\beta$ [c] | Gelation time [d] (min) |
|---|---|---|---|---|---|---|
| 1 | 120.80 | 2.64 | 951.40 | 27.75 | 45.76 | 2.58 ± 0.27 |
| 2 | 60.40 | 1.32 | 475.70 | 27.75 | 45.76 | 3.11 ± 0.10 |
|   |   |   |   |   |   | (5.11 ± 0.14) [e] |
| 3 | 60.40 | 1.32 | 475.70 | 27.75 | 45.76 | 0.97 ± 0.04 [f] |
| 4 | 20.133 | 0.44 | 158.57 | 27.75 | 45.76 | 7.15 ± 0.34 |
| 5 | 12.08 | 0.264 | 95.14 | 27.75 | 45.76 | 40.89 ± 1.14 |

TABLE 1-continued

Effects of the initial concentrations of HONB, H$_2$O$_2$, and HRP on gelation time [a]

| Entry | [HONB] (mM) | [H$_2$O$_2$] (mM) | [HRP] × 10$^4$ (mM) | α [b] | β [c] | Gelation time [d] (min) |
|---|---|---|---|---|---|---|
| 6 | 60.40 | 0.44 | 95.14 | 46.25 | 137.27 | 8.02 ± 0.92 (12.84 ± 0.19) [e] |
| 7 | 30.20 | 0.22 | 47.57 | 46.25 | 137.27 | 21.81 ± 1.27 |
| 8 | 60.40 | 1.32 | 95.14 | 138.75 | 45.76 | 23.73 ± 0.79 (37.64 ± 0.85) [e] |
| 9 | 60.40 | 1.32 | 47.57 | 277.50 | 45.76 | 58.78 ± 4.12 |
| 10 | 60.40 | 1.32 | 23.79 | 555.00 | 45.76 | 205.36 ± 12.38 |
| 11 | 60.40 | 0.44 | 47.57 | 92.50 | 137.27 | 18.50 ± 0.36 (29.54 ± 0.77) [e] |
| 12 | 60.40 | 0.44 | 23.79 | 185.00 | 137.27 | 56.00 ± 2.84 |
| 13 | 60.40 | 26.40 | 475.70 | 555.00 | 2.29 | 149.23 ± 1.99 |
| 14 | 60.40 | 10.00 | 475.70 | 210.23 | 6.04 | 71.56 ± 0.47 |
| 15 | 60.40 | 0.44 | 475.70 | 9.25 | 137.27 | 3.52 ± 0.29 |
| 16 | 60.40 | 0.33 | 475.70 | 6.94 | 183.04 | 24,655.00 ± 222.00 |
| 17 | 12.08 | 2.64 | 158.57 | 166.50 | 4.58 | 67.28 ± 3.91 |
| 18 | 16.11 | 3.52 | 158.57 | 222.00 | 4.58 | 82.50 ± 1.83 |
| 19 | 60.40 | 13.20 | 158.57 | 832.40 | 4.58 | 324.93 ± 4.70 |
| 20 | 271.80 | 59.40 | 158.57 | 3,746.25 | 4.58 | 666.07 ± 12.68 |
| 21 | 20.13 | 1.32 | 158.57 | 83.24 | 15.25 | 17.50 ± 0.38 |
| 22 | 40.41 | 2.65 | 158.57 | 167.17 | 15.25 | 36.42 ± 0.59 |
| 23 | 67.10 | 4.40 | 158.57 | 277.50 | 15.25 | 89.14 ± 2.97 |
| 24 | 60.40 | 1.32 | 475.70 | 27.75 | 45.76 | 1.93 ± 0.05 [g] |

[a] Conditions: [PEGDA] = 87.2 mM; [DMA] = 402.7 mM; 22° C.
[b] α is defined as the ratio of the initial molar concentration of H$_2$O$_2$ to that of HRP (i.e., [H$_2$O$_2$]/[HRP]).
[c] β is defined as the ratio of the initial molar concentration of HONB to that of H$_2$O$_2$ (i.e., [HONB]/[H$_2$O$_2$]).
[d] Determined by vial inversion test.
[e] Determined by rheological measurement.
[f] Conditions: [PEGDA] = 87.2 mM; [NVP] = 388.3 mM; 22° C.
[g] Conditions: [4-arm-PEG10K-acrylate] = 4.0 mM; [NVP] = 467.9 mM; 22° C. All data are mean ± s.d. Sample size n = 3 except for Entry 1 (n = 6), Entry 6 (n = 8), Entry 14 (n = 5), Entry 21 (n = 5), and Entry 24 (n = 4).

TABLE 2

Effect of β on gelation time [a]

| Entry | [HONB] (mM) | [H$_2$O$_2$] (mM) | [HRP] × 10$^4$ (mM) | α [b] | β [c] | Gelation time [d] (min) |
|---|---|---|---|---|---|---|
| 1 | 320.12 | 0.44 | 158.57 | 27.75 | 727.55 | n.d. [e] |
| 2 | 314.08 | 0.44 | 158.57 | 27.75 | 713.82 | 473.60 ± 7.91 |
| 3 | 308.04 | 0.44 | 158.57 | 27.75 | 700.09 | 330.94 ± 15.87 |
| 4 | 302.00 | 0.44 | 158.57 | 27.75 | 686.36 | 18.02 ± 0.63 |
| 5 | 286.90 | 0.44 | 158.57 | 27.75 | 652.05 | 15.85 ± 0.47 |
| 6 | 286.60 | 0.44 | 158.57 | 27.75 | 651.36 | 10.47 ± 0.38 |
| 7 | 286.30 | 0.44 | 158.57 | 27.75 | 650.68 | 6.66 ± 0.12 |
| 8 | 283.88 | 0.44 | 158.57 | 27.75 | 645.22 | 6.12 ± 0.27 |
| 9 | 277.84 | 0.44 | 158.57 | 27.75 | 631.45 | 6.37 ± 0.38 |
| 10 | 271.80 | 0.44 | 158.57 | 27.75 | 617.73 | 5.93 ± 0.20 |
| 11 | 241.60 | 0.44 | 158.57 | 27.75 | 549.09 | 5.68 ± 0.11 |
| 12 | 181.20 | 0.44 | 158.57 | 27.75 | 411.82 | 5.63 ± 0.36 |
| 13 | 120.80 | 0.44 | 158.57 | 27.75 | 274.55 | 5.44 ± 0.28 |
| 14 | 60.40 | 0.44 | 158.57 | 27.75 | 137.27 | 4.96 ± 0.08 |
| 15 | 40.27 | 0.44 | 158.57 | 27.75 | 91.52 | 5.63 ± 0.27 |
| 16 | 20.133 | 0.44 | 158.57 | 27.75 | 45.76 | 7.15 ± 0.34 |
| 17 | 12.08 | 0.44 | 158.57 | 27.75 | 27.45 | 8.81 ± 0.22 |
| 18 | 8.63 | 0.44 | 158.57 | 27.75 | 19.61 | 17.03 ± 0.87 |
| 19 | 8.57 | 0.44 | 158.57 | 27.75 | 19.48 | 813.83 ± 34.57 |
| 20 | 8.51 | 0.44 | 158.57 | 27.75 | 19.34 | 17,279.67 ± 297.72 |
| 21 | 8.39 | 0.44 | 158.57 | 27.75 | 19.07 | 18,639.33 ± 453.69 |
| 22 | 8.27 | 0.44 | 158.57 | 27.75 | 18.80 | 19,214.10 ± 449.04 |
| 23 | 8.05 | 0.44 | 158.57 | 27.75 | 18.30 | 21,656.70 ± 1,256.70 |

[a] Conditions: [PEGDA] = 87.2 mM; [DMA] = 402.7 mM; 22° C.
[b] α is defined as the ratio of the initial molar concentration of H$_2$O$_2$ to that of HRP (i.e., [H$_2$O$_2$]/[HRP]).
[c] β is defined as the ratio of the initial molar concentration of HONB to that of H$_2$O$_2$ (i.e., [HONB]/[H$_2$O$_2$]).
[d] Determined by vial inversion test.
[e] Not detectable. All data are mean ± s.d. Sample size n = 3 except for Entry 4 (n = 5), Entry 11 (n = 4), Entry 12 (n = 4), Entry 14 (n = 5), and Entry 18 (n = 5).

TABLE 3

The pH values of precursor solutions with different HONB concentrations [a]

| | HONB concentration (mM) | | | | |
|---|---|---|---|---|---|
| | 12.08 | 30.20 | 60.40 | 181.20 | 302.00 |
| pH | 4.36 ± 0.04 | 3.98 ± 0.04 | 3.81 ± 0.03 | 3.49 ± 0.03 | 3.30 ± 0.03 |

[a] Conditions: [PEGDA] = 87.2 mM; [DMA] = 402.7 mM; no $H_2O_2$ was added; 22° C. All data are mean ± s.d.

One skilled in the art will readily appreciate that the present disclosure is well adapted to carry out the objects and obtain the ends and advantages mentioned, as well as those inherent therein. The present disclosure described herein is presently representative of preferred embodiments, is exemplary, and is not intended as a limitation on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or descriptions found in the cited references.

The invention claimed is:

1. A method for making a polymer, comprising:
   (a) providing a composition comprising a vinyl monomer, N-hydroxy-5-norbornene-2,3-dicarboximide (HONB), horseradish peroxidase (HRP), and hydrogen peroxide ($H_2O_2$); and
   (b) incubating the composition to provide the polymer.

2. The method of claim 1, wherein the composition comprises $H_2O_2$ and HRP in a molar ratio of about 5 to about 4000.

3. The method of claim 1, wherein the composition comprises HONB and $H_2O_2$ in a molar ratio of about 1 to about 800.

4. The method of claim 1, wherein the composition comprises HONB at a concentration of at least about 8 mM.

5. The method of claim 1, wherein the composition comprises $H_2O_2$ at a concentration of at least about 0.2 mM.

6. The method of claim 1, wherein the composition further comprises an aqueous solution, wherein the aqueous solution has a pH of about 1 to about 8.

7. The method of claim 1, wherein step (a) comprises: (i) providing a first mixture of the vinyl monomer in an aqueous solution, and (ii) adding HONB, HRP, and $H_2O_2$ to the first mixture to provide the composition.

8. The method of claim 1, wherein step (a) comprises: (i) providing a first mixture of HONB and $H_2O_2$, and (ii) adding HRP to the first mixture to provide the composition.

9. The method of claim 1, wherein the polymer is a hydrogel.

10. The method of claim 1, wherein the vinyl monomer is selected from (meth) acrylamide monomers, (meth) acrylate monomers, N-vinyl lactam monomers, and combinations thereof.

11. The method of claim 10, wherein the vinyl monomer is selected from acrylamide, methacrylamide, N,N-dimethyl acrylamide, N-isopropyl acrylamide, hydroxyethyl acrylate, poly (ethylene glycol) methyl ether acrylate, poly (ethylene glycol) methyl ether methacrylate, 2-hydroxypropyl methacrylamide, 2-hydroxyethyl methacrylate, 2-methoxyethyl acrylate, methacrylic acid, 4-acryloylmorpholine, dimethyl vinylphosphonate, N-vinylcaprolactam, N-vinyl pyrrolidone, and combinations thereof.

12. The method of claim 1, wherein the composition further comprises a crosslinker selected from poly (ethylene glycol) diacrylate, poly (ethylene glycol) dimethacrylate, gelatin methacryloyl, acryloylated proteins, N,N'-methylene-bisacrylamide, bisphenol A glycerolate diacrylate, multi-arm acrylate-terminated poly (ethylene glycol), and combinations thereof.

13. The method of claim 12, wherein the crosslinker is 4-arm-PEG10K-acrylate.

14. The method of claim 1, wherein the composition further comprises one or more water-dispersible inorganic nanomaterials selected from gold nanoparticles, silica nanoparticles, and hydroxyapatite nanoparticles.

15. The method of claim 1, wherein the method is carried out at a temperature ranging from about 15° C. to about 37° C.

16. The method of claim 1, wherein the method is carried out in an open reaction vessel.

17. The method of claim 1, wherein the method is carried out in a closed reaction vessel.

18. An enzyme-mediated radical initiating system, wherein the system comprises N-hydroxy-5-norbornene-2,3-dicarboximide (HONB), horseradish peroxidase (HRP), and hydrogen peroxide ($H_2O_2$).

19. A kit comprising: N-hydroxy-5-norbornene-2,3-dicarboximide (HONB), horseradish peroxidase (HRP), and hydrogen peroxide ($H_2O_2$).

20. The kit of claim 19, further comprising at least one of: a container, a vinyl monomer, a crosslinker, and instructions for carrying out a polymerization reaction.

* * * * *